US011571561B2

(12) United States Patent
Quinnell et al.

(10) Patent No.: US 11,571,561 B2
(45) Date of Patent: Feb. 7, 2023

(54) MODULAR ELECTRICAL THERAPY DEVICE

(71) Applicant: ZOLL MEDICAL CORPORATION, Chelmsford, MA (US)

(72) Inventors: Scott D. Quinnell, Kittanning, PA (US); Brian D. Snyder, Pittsburgh, PA (US); Robert J. Hulings, Mars, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 213 days.

(21) Appl. No.: 17/061,727

(22) Filed: Oct. 2, 2020

(65) Prior Publication Data
US 2021/0106811 A1    Apr. 15, 2021

Related U.S. Application Data

(60) Provisional application No. 62/912,896, filed on Oct. 9, 2019.

(51) Int. Cl.
| | | |
|---|---|---|
| *A61N 1/04* | (2006.01) | |
| *A61N 1/36* | (2006.01) | |
| *A61N 1/44* | (2006.01) | |

(52) U.S. Cl.
CPC ........ *A61N 1/0472* (2013.01); *A61N 1/36014* (2013.01); *A61N 1/44* (2013.01)

(58) Field of Classification Search
CPC ... A61N 1/36014; A61N 1/044; A61N 1/0472
See application file for complete search history.

(56) References Cited

U.S. PATENT DOCUMENTS

| | | |
|---|---|---|
| 4,094,310 A | 6/1978 | McEachern et al. |
| 4,632,122 A | 12/1986 | Johansson et al. |

(Continued)

FOREIGN PATENT DOCUMENTS

| | | |
|---|---|---|
| DE | 2644236 C3 | 4/1981 |
| EP | 0 459 239 A2 | 12/1991 |

(Continued)

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.

(Continued)

*Primary Examiner* — Alyssa M Alter
(74) *Attorney, Agent, or Firm* — Lando & Anastasi, LLP

(57) ABSTRACT

A therapeutic electrode component includes a base plate having a first side and a second side having a conductive surface. A repository having an internal volume to releasably retain a conductive fluid is disposed on the first side of the base plate. A rupturable membrane is disposed between the internal volume of the repository and the conductive surface of the base plate. A coupling is disposed on the base plate that is configured to detachably engage a gas charge, whereby the gas charge is detachable from the coupling without causing destruction of the gas charge, to provide a hermetic seal with an outlet of the gas charge, and to provide fluid communication between the internal volume of the repository and the outlet of gas charge when the gas charge is engaged by the coupling. A retainer is configured to detachably secure the gas charge to the base plate.

26 Claims, 26 Drawing Sheets

(56) References Cited

U.S. PATENT DOCUMENTS

| | | |
|---|---|---|
| 4,928,690 A | 5/1990 | Heilman et al. |
| 4,978,926 A | 12/1990 | Zerod et al. |
| 5,062,834 A | 11/1991 | Gross et al. |
| 5,078,134 A * | 1/1992 | Heilman ............... A61N 1/046 |
| | | 607/142 |
| 5,348,008 A | 9/1994 | Bornn et al. |
| 5,357,696 A | 10/1994 | Gray et al. |
| 5,365,932 A | 11/1994 | Greenhut |
| 5,472,453 A | 12/1995 | Alt |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,532,379 B2 | 3/2003 | Stratbucker |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,908,437 B2 | 6/2005 | Bardy |
| 6,944,498 B2 | 9/2005 | Owen et al. |
| 6,990,373 B2 | 1/2006 | Jayne et al. |
| 7,074,199 B2 | 7/2006 | Halperin et al. |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,149,579 B1 | 12/2006 | Koh et al. |
| 7,220,235 B2 | 5/2007 | Geheb et al. |
| 7,295,871 B2 | 11/2007 | Halperin et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,522,951 B2 | 4/2009 | Gough et al. |
| 7,831,303 B2 | 11/2010 | Rueter et al. |
| 7,974,689 B2 | 7/2011 | Volpe et al. |
| 3,121,683 A1 | 2/2012 | Bucher et al. |
| 8,140,154 B2 | 3/2012 | Donnelly et al. |
| 8,271,082 B2 | 9/2012 | Donnelly et al. |
| 9,008,801 B2 | 4/2015 | Kaib et al. |
| 9,427,564 B2 | 8/2016 | Kaib et al. |
| 9,457,178 B2 | 10/2016 | Kaib et al. |
| 9,956,392 B2 | 5/2018 | Kaib et al. |
| 10,183,160 B2 | 1/2019 | Kaib et al. |
| 2003/0004547 A1 | 1/2003 | Owen et al. |
| 2003/0055460 A1 | 3/2003 | Owen et al. |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2004/0007970 A1 | 1/2004 | Ma et al. |
| 2004/0162510 A1 | 8/2004 | Jayne et al. |
| 2004/0249419 A1 | 12/2004 | Chapman et al. |
| 2005/0049515 A1 | 3/2005 | Misczynski et al. |
| 2005/0131465 A1 | 6/2005 | Freeman et al. |
| 2006/0036292 A1 | 2/2006 | Smith et al. |
| 2006/0085049 A1 | 4/2006 | Cory et al. |
| 2006/0211934 A1 | 9/2006 | Hassonjee et al. |
| 2006/0220809 A1 | 10/2006 | Stigall et al. |
| 2006/0264776 A1 | 11/2006 | Stahmann et al. |
| 2006/0270952 A1 | 11/2006 | Freeman et al. |
| 2007/0028821 A1 | 2/2007 | Bennett et al. |
| 2007/0060993 A1 | 3/2007 | Craige et al. |
| 2007/0073120 A1 | 3/2007 | Li et al. |
| 2007/0118056 A1 | 5/2007 | Wang et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0021532 A1 | 1/2008 | Kveen et al. |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0249591 A1 | 10/2008 | Gaw et al. |
| 2008/0306560 A1 | 12/2008 | Macho et al. |
| 2008/0306562 A1 | 12/2008 | Donnelly et al. |
| 2008/0306566 A1 | 12/2008 | Holmstrom et al. |
| 2008/0312709 A1 | 12/2008 | Volpe et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0088652 A1 | 4/2009 | Tremblay |
| 2009/0093687 A1 | 4/2009 | Telfort et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0234716 A1 | 9/2010 | Engel |
| 2010/0298899 A1 | 11/2010 | Donnelly et al. |
| 2011/0077728 A1 | 3/2011 | Li et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2016/0271384 A1 * | 9/2016 | Kaib ..................... A61N 1/046 |
| 2019/0160278 A1 | 5/2019 | Volosin et al. |
| 2022/0249854 A1 | 8/2022 | Ballard et al. |

FOREIGN PATENT DOCUMENTS

| | | |
|---|---|---|
| EP | 0295497 B1 | 9/1993 |
| EP | 0335356 B1 | 3/1996 |
| EP | 1455640 B1 | 1/2008 |
| EP | 2083104 A2 | 7/2009 |
| EP | 1720446 B1 | 7/2010 |
| JP | 5115450 A | 5/1993 |
| JP | 2006510431 A | 3/2006 |
| JP | 2006512128 A | 4/2006 |
| JP | 2006223168 A | 8/2006 |
| JP | 2009510276 A | 3/2009 |
| WO | 200002484 A1 | 1/2000 |

(56) References Cited

FOREIGN PATENT DOCUMENTS

| WO | 2004054656 A1 | 7/2004 |
| WO | 2006050235 A1 | 5/2006 |
| WO | 20070057169 A1 | 5/2007 |
| WO | 2007077997 A1 | 7/2007 |
| WO | 2015056262 A1 | 4/2015 |
| WO | 2016149450 A1 | 9/2016 |

OTHER PUBLICATIONS

DeBock et al., "Captopril treatment of chronic heart failure in the very old," J. Gerontol. (1994) 49: M148-M152.
http://www.web.archive.org/web/20030427001846/http:/www.lifecor.com/imagelib/imageproduct.asp.Published by LifeCor, Inc., 2002, on a webpage owned by LifeCor, Inc.
O'Keeffe et al., "Reproducability and responsiveness of quality of the assessment and six minute walk test in elderly heart failure patients," Heart (1998) 80: 377-382.
Extended European Search Report from European Application No. 20200825.6 dated Mar. 3, 2021.

\* cited by examiner

MODULAR ELECTRICAL THERAPY DEVICE

CROSS-REFERENCE TO RELATED APPLICATIONS

This application claims priority under 35 U.S.C. § 119(e) to U.S. Provisional Patent Application Ser. No. 62/912,896, titled MODULAR ELECTRICAL THERAPY DEVICE, filed Oct. 9, 2019, the content of which is incorporated herein by reference for all purposes.

BACKGROUND

The present disclosure is generally directed to systems and methods of delivering electrical therapy to a patient.

There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some examples, physicians may use medical devices alone or in combination with drug therapies to treat conditions such as cardiac arrhythmias.

One of the deadliest cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (e.g., heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

Some examples of cardiac monitoring and/or treatment devices include therapy electrodes that release conductive gel onto the skin of a subject prior to delivering electrical therapy to the subject to decrease electrical resistance between the therapy electrode and the subject. Such therapy electrodes have in the past been single use devices that would be replaced after each use with the older devices being discarded.

SUMMARY

In accordance with one aspect, there is provided a therapeutic electrode component for application of electrical stimulus to a subject and for allowing reuse of non-destroyed portions of a therapeutic electrode in application of electrical stimulus to a subject. The therapeutic electrode component comprises a base plate having a first side and a second side opposing the first side, the second side having a conductive surface. The therapeutic electrode component further comprises a repository having an internal volume configured to releasably retain a conductive fluid. The repository is disposed on the first side of the base plate. A rupturable membrane is disposed between the internal volume of the repository and the conductive surface of the base plate. A coupling is disposed on the base plate. The coupling is configured to detachably engage a gas charge, whereby the gas charge is detachable from the coupling without causing destruction of at least the gas charge, to provide a hermetic seal with an outlet of the gas charge, and to provide fluid communication between the internal volume of the repository and the outlet of gas charge when the gas charge is engaged by the coupling. The therapeutic electrode component further comprises a retainer configured to detachably secure the gas charge to the base plate.

In some embodiments, the gas charge is detachable from the coupling without causing destruction of at least the base plate, the repository, and the rupturable membrane.

In some embodiments, the coupling comprises a barb including an internal pneumatic conduit configured to provide the fluid communication between the internal volume of the repository and the outlet of gas charge when the gas charge is engaged by the coupling.

In some embodiments, the therapeutic electrode component further comprises a connector formed of a resilient material and including a conduit having a first opening configured to receive and releasably retain the barb and a second opening configured to receive and retain the outlet of the gas charge.

In some embodiments, the therapeutic electrode component further comprises pneumatic tubing providing fluid communication between the outlet of the gas charge and the barb.

In some embodiments, the barb extends in a direction parallel to a plane defined by a surface of the first side of the base plate.

In some embodiments, the barb extends in a direction perpendicular to a plane defined by a surface of the first side of the base plate.

In some embodiments, the coupling comprises a snap ring coupled to the first side of the base plate. The therapeutic electrode component may further comprise a feed-through including a base that surrounds an end portion of the gas charge and the outlet of the gas charge, and a barb extending from the base that is configured to releasably engage the snap ring. The therapeutic electrode component may further comprise an O-ring disposed between the base and the snap ring when the barb is engaged with the snap ring and that enhances hermeticity of a seal between the feed-through and snap ring.

In some embodiments, the therapeutic electrode component further comprises a pneumatic header in fluid communication with the outlet of the gas charge, the snap ring being configured to receive and releasably retain the pneumatic header. The therapeutic electrode component may further comprise an O-ring disposed between the snap ring and pneumatic header when the gas charge is engaged with the coupling and that enhances hermeticity of a seal between the snap ring and pneumatic header. The pneumatic header may be retained within a resilient body coupled to the gas charge.

In some embodiments, the coupling comprises a feed-though disposed on the first side of the base plate including a neck defining an internal volume. The therapeutic electrode component may further comprise a washer formed of a resilient material that surrounds a length of the outlet of the gas charge and is configured to be retained within the internal volume of the neck of the feed-thorough, an O-ring surrounding the neck of the feed-through, and a snap ring that couples to the feed through and traps the O-ring between the snap ring and the feed-through.

In some embodiments, the gas charge is disposed within a module that is detachably engageable with the base plate. The coupling may include a post disposed on the first side of the base plate and including a pneumatic conduit configured to provide the fluid communication between the internal volume of the repository and the outlet of gas charge when the gas charge is engaged by the coupling. The post may be configured to engage an aperture in the module. The therapeutic electrode component may further comprise an O-ring disposed between a neck of the pneumatic conduit and the aperture in the module that enhances hermeticity of a seal between the pneumatic conduit and module. The module may be configured to couple to the first side of the base plate by sliding the module in a plane defined by a surface of the first side of the base plate into a cradle coupled to the first side of the base plate. The retainer may include one or more clips disposed on the cradle that engage one or more slots on the module. The retainer may include one or more clips disposed on the module that engage one or more slots on the cradle. The retainer may include one or more conductive fasteners that pass through the base plate and engage one or more respective apertures in the module. The one or more conductive fasteners may electrically engage the conductive surface of the base plate when securing the module to the base plate. The one or more conductive fasteners may be configured to deliver one of a defibrillation pulse or a pacing pulse to the subject through the conductive surface of the base plate. In some examples, the defibrillation pulse may include a biphasic current pulse of between about 0 and 150 A. In some embodiments, the therapeutic electrode component further comprises a circuit board disposed within the module and configured to control activation of the gas charge. The therapeutic electrode component may further comprise signal leads in electrical communication between the circuit board and the gas charge and configured to deliver an activation current to the gas charge. In some examples, the activation current may be at least 0.1 mA.

In some embodiments, the module is configured to couple to the first side of the base plate by moving the module in a direction perpendicular to a plane defined by a surface of the first side of the base plate onto the first side of the base plate.

In some embodiments, the therapeutic electrode component further comprises a conduit disposed on the base plate providing fluid communication between the coupling and the internal volume of the repository. The rupturable membrane may be configured to rupture responsive to delivery of gas from the gas charge to the internal volume of the repository through the conduit. The repository may be configured to release the conductive fluid onto the conductive surface of the base plate responsive to delivery of gas from the gas charge to the internal volume of the repository through the conduit. The repository may comprise a plurality of separate chambers each releasably retaining a volume of the conductive fluid and in fluid communication with the conduit.

In accordance with another aspect, there is provided a wearable therapeutic device for allowing reuse of non-destroyed portions of a therapeutic electrode in application of electrical stimulus to a subject. The device comprises a garment configured to be worn about the subject, at least one therapeutic electrode component configured to be removably retained by the garment, circuitry configured to provide a therapeutic pulse of energy to the at least one therapeutic electrode component, and at least one processor operatively coupled to the circuitry and the at least one therapeutic electrode component. The at least one therapeutic component comprises a base plate having a first side and a second side opposing the first side. The second side has a conductive surface. The at least one therapeutic component further comprises a repository having an internal volume configured to releasably retain the conductive fluid. The repository is disposed on the first side of the base plate. A rupturable membrane is disposed between the internal volume of the repository and the conductive surface of the base plate. A coupling is disposed on the base plate. The coupling is configured to detachably engage a gas charge, whereby the gas charge is detachable from the coupling without causing destruction of at least the gas charge, to provide a hermetic seal with an outlet of the gas charge, and to provide fluid communication between the internal volume of the repository and the outlet of gas charge when the gas charge is engaged by the coupling. The at least one therapeutic component further comprises a retainer configured to detachably secure the gas charge to the base plate.

In accordance with another aspect, there is provided a method for delivery of electrical stimulus to a subject and allowing reuse of non-destroyed portions of a therapeutic electrode in application of the electrical stimulus to the subject. The method comprises securing a gas charge to a coupling disposed on a first surface of a base plate of a therapeutic electrode component, the coupling providing fluid communication with an internal volume of a repository disposed on the base plate, the repository configured to dispense a conductive fluid onto a conductive second surface of the base plate through a rupturable membrane disposed between the internal volume of the repository and the conductive surface of the base plate. The method further comprises, responsive to determining that the gas charge should be replaced, removing the gas charge from the coupling without causing destruction to at least the base plate, the repository, and the rupturable membrane, and securing a replacement gas charge to the coupling.

In accordance with another aspect, there is provided a method for delivery of electrical stimulus to a subject and allowing reuse of non-destroyed portions of a therapeutic electrode in delivery of the electrical stimulus to the subject. The method comprises securing a gas charge to a coupling disposed on a first surface of a base plate of a therapeutic electrode component, the coupling providing fluid communication with an internal volume of a repository disposed on the base plate, the repository configured to dispense a conductive fluid onto a conductive second surface of the base plate through a rupturable membrane disposed between the internal volume of the repository and the conductive surface of the base plate. The method further comprises, responsive to determining that the gas charge should be moved from the therapeutic electrode component to a second therapeutic electrode component, removing the gas charge from the coupling without causing destruction to at least the base plate, the repository, and the rupturable membrane, and securing the gas charge to a second coupling of the second therapeutic electrode component.

In accordance with another aspect, there is provided a therapeutic electrode component for application of electrical stimulus to a subject and for allowing reuse of non-destroyed portions of a therapeutic electrode in application of electrical stimulus to a subject. The therapeutic electrode component comprises a base plate having a first side and a second side opposing the first side, the second side having a conductive surface. The therapeutic electrode component further comprises a repository having an internal volume configured to releasably retain a conductive fluid. The repository is disposed on the first side of the base plate. A rupturable membrane is disposed between the internal volume of the repository and the conductive surface of the base plate. A coupling is disposed on the base plate. The coupling is configured to detachably engage a gas charge. The gas charge is detachable from the coupling without causing destruction of at least the gas charge and/or the coupling. The coupling provides a hermetic seal with an outlet of the gas charge, and fluid communication between the internal volume of the repository and the outlet of gas charge when the gas charge is engaged by the coupling. The therapeutic electrode component further comprises a retainer configured to detachably secure the gas charge to the base plate.

In accordance with another aspect, there is provided a therapeutic electrode component for application of electrical stimulus to a subject and for allowing reuse of non-destroyed portions of a therapeutic electrode in application of electrical stimulus to a subject. The therapeutic electrode component comprises a base plate having a first side and a second side opposing the first side, the second side having a conductive surface, a repository having an internal volume configured to releasably retain a conductive fluid, the repository disposed on the first side of the base plate, a rupturable membrane disposed between the internal volume of the repository and the conductive surface of the base plate, a coupling disposed on the base plate, the coupling configured to detachably engage a gas charge, the gas charge being detachable from the coupling without causing destruction of at least the gas charge, the coupling further configured to provide a hermetic seal with an outlet of the gas charge, and to provide fluid communication between the internal volume of the repository and the outlet of gas charge when the gas charge is engaged by the coupling, and a retainer configured to detachably secure the gas charge to the base plate.

In some embodiments, the gas charge is detachable from the coupling without causing destruction of at least the base plate, the repository, and the rupturable membrane.

In some embodiments, the coupling comprises a barb including an internal pneumatic conduit configured to provide the fluid communication between the internal volume of the repository and the outlet of gas charge when the gas charge is engaged by the coupling.

In some embodiments, the therapeutic electrode component further comprises a connector formed of a resilient material and including a conduit having a first opening configured to receive and releasably retain the barb and a second opening configured to receive and retain the outlet of the gas charge.

In some embodiments, the coupling comprises a snap ring coupled to the first side of the base plate, and a pneumatic header in fluid communication with the outlet of the gas charge, the snap ring being configured to releasably retain the pneumatic header.

In some embodiments, the pneumatic header is retained within a resilient body coupled to the gas charge.

In some embodiments, the coupling comprises a feed-though disposed on the first side of the base plate including a neck defining an internal volume, a washer formed of a resilient material that surrounds a length of the outlet of the gas charge and is configured to be retained within the internal volume of the neck of the feed-thorough, an O-ring surrounding the neck of the feed-through, and a snap ring that couples to the feed through and traps the O-ring between the snap ring and the feed-through.

In some embodiments, the gas charge is disposed within a module that is detachably engageable with the base plate, and the coupling includes a post disposed on the first side of the base plate and including a pneumatic conduit configured to provide the fluid communication between the internal volume of the repository and the outlet of gas charge when the gas charge is engaged by the coupling, the post configured to engage an aperture in the module.

In some embodiments, the gas charge is disposed within a module that is detachably engageable with the base plate, and wherein the module is configured to couple to the first side of the base plate by sliding the module in a plane defined by a surface of the first side of the base plate into a cradle coupled to the first side of the base plate.

In some embodiments, the retainer includes one or more conductive fasteners that pass through the base plate and engage one or more respective apertures in the module.

In some embodiments, the one or more conductive fasteners electrically engage the conductive surface of the base plate when securing module to the base plate.

In some embodiments, the therapeutic electrode component further comprises one or more conductive fasteners, the one or more conductive fasteners configured to deliver one of a defibrillation pulse or a pacing pulse to the subject through the conductive surface of the base plate.

In some embodiments, the defibrillation pulse comprises a biphasic current pulse of between about 0 and 150 Amps and the pacing pulse comprises a current of between about 0 mAmps to about 200 to mAmps.

In some embodiments, the gas charge is disposed within a module that is detachably engageable with the base plate, and the therapeutic electrode component further comprises a circuit board disposed within the module and configured to control activation of the gas charge, and signal leads in electrical communication between the circuit board and the gas charge and configured to deliver an activation current to the gas charge.

In some embodiments, the gas charge is disposed within a module that is detachably engageable with the base plate, the module being configured to couple to the first side of the base plate by moving the module in a direction perpendicular to a plane defined by a surface of the first side of the base plate on to the first side of the base plate.

In some embodiments, the therapeutic electrode component further comprises a conduit disposed on the base plate providing fluid communication between the coupling and the internal volume of the repository.

In some embodiments, the repository comprises a plurality of separate chambers each releasably retaining a volume of the conductive fluid and in fluid communication with the conduit.

In some embodiments, the rupturable membrane is configured to rupture responsive to delivery of gas from the gas charge to the internal volume of the repository through the conduit.

In some embodiments, the repository is configured to release the conductive fluid onto the conductive surface of the base plate responsive to delivery of gas from the gas charge to the internal volume of the repository through the conduit.

In accordance with another aspect, there is provided a wearable therapeutic device for allowing reuse of non-destroyed portions of a therapeutic electrode in application of electrical stimulus to a subject. The wearable therapeutic device comprises a garment configured to be worn about the subject, at least one therapeutic electrode component configured to be removably retained by the garment, circuitry configured to provide a therapeutic pulse of energy to the at least one therapeutic electrode component, and at least one processor operatively coupled to the circuitry and the at least one therapeutic electrode component. The at least one therapeutic component comprises a base plate having a first side and a second side opposing the first side, the second side having a conductive surface, a repository having an internal volume configured to releasably retain the conductive fluid, the repository disposed on the first side of the base plate, a rupturable membrane disposed between the internal volume of the repository and the conductive surface of the base plate, a coupling disposed on the base plate, the coupling configured to detachably engage a gas charge, the gas charge being detachable from the coupling without causing destruction of at least the gas charge, the coupling further configured to provide a hermetic seal with an outlet of the gas charge, and to provide fluid communication between the internal volume of the repository and the outlet of gas charge when the gas charge is engaged by the coupling, an a retainer configured to detachably secure the gas charge to the base plate.

In some embodiments, the gas charge is detachable from the coupling without causing destruction of at least the base plate, the repository, and the rupturable membrane.

In some embodiments, the wearable therapeutic device further comprises one or more conductive fasteners, the one or more conductive fasteners configured to deliver one of a defibrillation pulse or a pacing pulse to the subject through the conductive surface of the base plate.

In some embodiments, the defibrillation pulse comprises a biphasic current pulse of between about 0 and 150 Amps and the pacing pulse comprises a current of between about 0 mAmps to about 200 to mAmps.

In some embodiments, the gas charge is disposed within a module that is detachably engageable with the base plate, and the therapeutic electrode component further comprises a circuit board disposed within the module and configured to control activation of the gas charge, and signal leads in electrical communication between the circuit board and the gas charge and configured to deliver an activation current to the gas charge.

In some embodiments, the wearable therapeutic device further comprises a conduit disposed on the base plate providing fluid communication between the coupling and the internal volume of the repository.

In some embodiments, the repository comprises a plurality of separate chambers each releasably retaining a volume of the conductive fluid and in fluid communication with the conduit.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
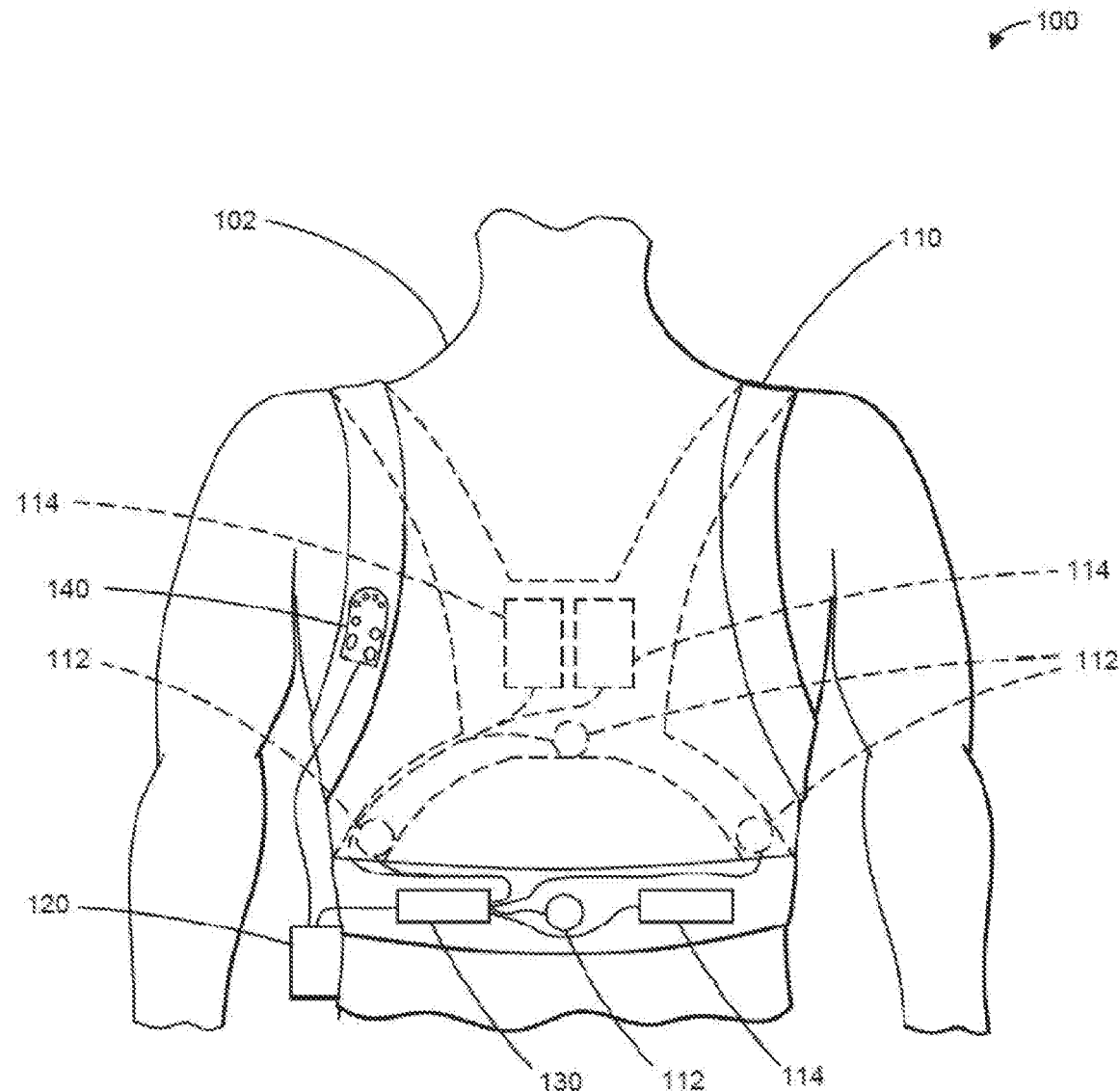
FIG. 1 depicts an example of a wearable medical device.

This disclosure relates to devices, systems and methods for delivering electrical therapy to a patient.

Cardiac monitoring and/or treatment devices include therapy electrode components that release conductive fluid or gel onto the skin of a subject prior to delivering electrical therapy. The gel causes a decrease in electrical resistance between the conductive surface of the therapy electrode and the subject's skin. The deployed gel can help avoid causing burns on the patient's skin during therapy. Further, the deployed gel can cause substantially all or most of the current from the therapeutic electrode components to be delivered to the patient. In implementation, the conductive fluid or gel may have a limited shelf life, for example, due to evaporation of liquid from the conductive fluid or gel. For example, such evaporation can occur through the walls of the receptacle(s) in the therapy electrode components that house the conductive fluid or gel prior to dispensing the fluid or gel. Example devices, systems, and methods are described herein to allow for reuse of non-destroyed portions of a therapeutic electrode. For example, during service, the deteriorated conductive fluid or gel can be removed and remaining therapeutic electrode components can be reused.

As described further below, one of the therapeutic electrode components that is designed herein to be re-used is a gas charge. A gas charge or cartridge is used in some examples of therapy electrode components to generate pressure to push the conductive fluid or gel out of the receptacle(s) in the therapy electrode components and onto the skin of a patient to reduce electrical resistance between the therapy electrode components and the patient. The gas cartridge can be, in some implementations, an expensive component of a therapy electrode. Conventional therapy electrode components including conductive fluid or gel dispensing systems gas cartridges utilizing gas cartridges as a source of pressure to dispense the conductive fluid or gel do not provide for the gas cartridge to be removed or replaced without damaging the gas cartridge or other portions of the therapy electrode component. Thus, in instances in which, for example, the conductive fluid or gel in a therapy electrode component reaches or exceeds its shelf life or if the therapy electrode component or gas cartridge develops a leak or some other defect that would warrant replacement of the gas cartridge, one cannot remove the gas cartridge and replace it or other portions of the therapy electrode component. Rather, the entire therapy electrode component, including the gas cartridge, is discarded. Example devices, systems, and methods are described herein to allow for reuse of non-destroyed portions of a therapeutic electrode. For example, during service, the deteriorated conductive fluid or gel can be removed and remaining therapeutic electrode components can be reused.

Examples of devices and systems for delivering electrical therapy to a patient disclosed herein include a therapeutic electrode component for application of electrical stimulus to a subject. The therapeutic electrode component allows for reuse of non-destroyed portions of a therapeutic electrode in application of electrical stimulus to a subject. In examples, the therapeutic electrode component includes a base plate having a first side and a second side opposing the first side. The second side of the therapeutic electrode component has a conductive surface that is disposed directly in contact with the skin of a patient, or indirectly such as through clothing, fabric, and/or a conductive mesh. The conductive surface may be disposed against, for example, a portion of the chest or back of the patient. Electrical therapy may be delivered to the patient through the conductive surface. The first side of the base plate includes a repository having an internal volume configured to releasably retain a conductive fluid that is expelled onto the skin of the patient and provides a low impedance electrical path between the conductive surface of the base plate and the skin of the patient to facilitate the delivery of the electrical therapy to the patient. A rupturable membrane is disposed between the internal volume of the repository and the conductive surface of the base plate which ruptures in response to pressure applied to the conductive fluid and allows the conductive fluid to be expelled onto the skin of the patient.

In implementations herein, a coupling is disposed on the base plate that allows one to detachably engage a gas charge to the base plate. The gas charge is used to provide the pressure to the conductive fluid when it is desired to expel the conductive fluid onto the skin of the subject. The gas charge is detachable from the coupling without causing destruction of at least the gas charge so that the gas charge may be replaced or removed for use with a different therapeutic electrode component. In examples, the coupling provides a hermetic seal with an outlet of the gas charge to prevent leaks of gas from the gas charge and to direct substantially all gas output from the gas charge to a portion of the therapeutic electrode component where it may apply pressure to the conductive fluid. The coupling, for example, provides fluid communication between the internal volume of the repository and the outlet of gas charge when the gas charge is engaged by the coupling. The therapeutic electrode component includes also includes a retainer configured to detachably secure the gas charge to the base plate.

Examples of systems for delivering electrical therapy to a patient disclosed herein may include a wearable therapeutic device that allows for reuse of non-destroyed portions of a therapeutic electrode component utilized for application of electrical stimulus to a subject. The wearable therapeutic device includes a garment configured to be worn about the subject. The garment is designed to removably retain at least one therapeutic electrode component as described above. The wearable therapeutic device includes circuitry that is used to provide a therapeutic pulse of energy to the at least one therapeutic electrode component. At least one processor is operatively coupled to the circuitry and the at least one therapeutic electrode component to control operation of the wearable therapeutic device and circuitry. The at least one therapeutic electrode component includes a base plate having a first side and a second side opposing the first side. The second side of the therapeutic electrode component has a conductive surface that may disposed against the skin of a patient directly, or indirectly such as through clothing, fabric, and/or a conductive mesh, for example, on a portion of the chest or back of the patient, and though which electrical therapy may be delivered to the patient. The first side of the base plate includes a repository having an internal volume configured to releasably retain a conductive fluid that is expelled onto the skin of the patient and provides a low impedance electrical path between the conductive surface of the base plate and the skin of the patient to facilitate the delivery of the electrical therapy to the patient. A rupturable membrane is disposed between the internal volume of the repository and the conductive surface of the base plate which ruptures in response to pressure applied to the conductive fluid and allows the conductive fluid to be expelled onto the skin of the patient. A coupling is disposed on the base plate that allows one to detachably engage a gas charge to the base plate. The gas charge is used to provide the pressure to the conductive fluid when it is desired to expel the conductive fluid onto the skin of the subject. The gas charge is detachable from the coupling without causing destruction of at least the gas charge so that the gas charge may be replaced or removed for use with a different therapeutic electrode component. The coupling provides a hermetic seal with an outlet of the gas charge to prevent leaks of gas from the gas charge and to direct substantially all gas output from the gas charge to a portion of the therapeutic electrode component where it may apply pressure to the conductive fluid. The coupling, for example, provides fluid communication between the internal volume of the repository and the outlet of gas charge when the gas charge is engaged by the coupling. The therapeutic electrode component includes also includes a retainer configured to detachably secure the gas charge to the base plate.

Examples of methods for delivery of electrical stimulus to a subject disclosed herein provide for reuse of non-destroyed portions of a therapeutic electrode component used to apply the electrical stimulus to the subject. In one example, the method includes securing a gas charge to a coupling disposed on a first surface of a base plate of a therapeutic electrode component. The coupling provides fluid communication with an internal volume of a repository disposed on the base plate. The repository includes conductive fluid which, prior to delivery of the electrical stimulus to the subject, is dispensed onto a conductive second surface of the base plate through a rupturable membrane disposed between the internal volume of the repository and the conductive surface of the base plate. If one determines that the gas charge should be replaced, for example, due to leakage or for use in a different therapeutic electrode component, the gas charge may be removed from the coupling without causing destruction to the gas charge, and in some examples, without causing damage to at least the base plate, the repository, and the rupturable membrane. One may then secure a replacement gas charge to the coupling or secure the gas charge to a coupling on a base plate of another therapeutic electrode component.

In another example, a method for delivery of electrical stimulus to a subject that allows for reuse of non-destroyed portions of a therapeutic electrode component used for delivery of the electrical stimulus to the subject includes securing a gas charge to a coupling disposed on a first surface of a base plate of a therapeutic electrode component. The coupling provides fluid communication with an internal volume of a repository disposed on the base plate. The repository is configured to dispense a conductive fluid onto a conductive second surface of the base plate through a rupturable membrane disposed between the internal volume of the repository and the conductive surface of the base plate. If one determines that the gas charge should be replaced, for example, to be moved from the therapeutic electrode component to a second therapeutic electrode component, one may remove the gas charge from the coupling without causing destruction to at least the base plate, the repository, and the rupturable membrane. One might desire to move the gas charge from a first therapeutic electrode component to another, for example if one the conductive fluid in the first therapeutic component is approaching or has exceeded its expiration date or if the hermeticity of the first therapeutic electrode component is in question and the gas charge is still expected to be useable. The method further includes securing the gas charge to a second coupling of the second therapeutic electrode component.

Advantages of various aspects and embodiments disclosed herein provide for the components of a therapy electrode component including a conductive fluid dispensation system to be non-destructively disassembled. In a therapy electrode component in which conductive fluid has expired, portions of the therapy electrode component, for example, the gas cartridge and/or circuit board and/or a module housing same may be removed, and one or more of these components may be installed onto a replacement base portion of the therapy electrode component including fresh conductive fluid. In another example, in a therapy electrode component in which the conductive gel and other associated components, for example, the base plate, conductive fluid repository, and rupturable membrane are all in useable condition, but the gas cartridge or circuit board are in some way defective, the gas cartridge and/or circuit board may be removed and replaced without damaging the base plate, conductive fluid repository, and rupturable membrane. Accordingly, portions of therapy electrode components may be replaced if desired to provide a functional therapy electrode component rather than disposing and replacing the entirety of the therapy electrode component.

Aspects and embodiment disclosed herein thus provide advantages with respect to cost and with respect to the number of replacement parts a user or supplier may keep on hand to maintain the therapy electrode components of a therapy electrode system of a patient in usable or optimal condition.

As described above, the teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device can be capable of continuous use by the patient. In some implementations, the continuous use can be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the therapy electrode components as described herein, during both periods of monitoring and periods when the device may not be monitoring the patient but is otherwise still worn by or otherwise attached to the patient. The wearable medical device can be configured to continuously monitor the patient for cardiac-related information (e.g., electrocardiogram (ECG) information, including arrhythmia information, heart sounds or heart vibrations, etc.) and/or non-cardiac information (e.g., blood oxygen, the patient's temperature, glucose levels, tissue fluid levels, and/or lung sounds or vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. The wearable medical device can be configured to monitor, for example, lung vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In examples, the device can output a defibrillation therapy in the form of a biphasic pulse of between about 0 and 150

Amps. For example, the biphasic waveform is a biphasic truncated exponential waveform. The device can be programmed to provide between around 75 joules to around 150 joules (±5%) at 20° C. (68° F.) when discharged into a 50 ohm resistive load. In implementations, settings within that range can be programmable in 25 joule increments. In an implementation, the device can be configured to deliver around 35 Amps for a maximum joule defibrillating shock delivered into a 50 ohm load. In examples, the defibrillation shock sequence can include between around 1 pulse to around 10 pulses. In examples, the sequence can include around 5 pulses. If conversion of the arrhythmia occurs after a shock, the device automatically precludes delivery of remaining shocks in the sequence. With respect to pacing therapy, in implementations, a maximum current level of current waveform may be set to a value between approximately 0 mAmps to 200 to mAmps. In examples, a pulse width may be set to a fixed value between approximately 0.05 ms to 2 ms. In examples, a frequency of the pulses may be set to a fixed value between approximately 30 pulses per minute (PPM) to approximately 200 PPM. In accordance with one implementation, a 40 ms square wave pulse may be used.

FIG. 1 illustrates an example of a medical device 100 that is external, ambulatory, and wearable by a patient 102, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. In one example scenario, such wearable defibrillators can be worn nearly continuously or substantially continuously for two to three months at a time. During the period of time in which it is worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114, a medical device controller 120, a connection pod 130, a patient interface pod 140, a belt, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and at least one of the therapy electrodes 114 can be included on a single integrated patch and adhesively applied to the patient's body.

The sensing electrodes 112 can be configured to detect one or more cardiac signals. Examples of such signals include ECG signals and/or other sensed cardiac physiological signals from the patient. In certain implementations, the sensing electrodes 112 can include additional components such as accelerometers, acoustic signal detecting devices, and other measuring devices for recording additional parameters. For example, the sensing electrodes 112 can also be configured to detect other types of patient physiological parameters and acoustic signals, such as tissue fluid levels, heart vibrations, lung vibrations, respiration vibrations, patient movement, etc. Example sensing electrodes 112 include a metal electrode with an oxide coating such as tantalum pentoxide electrodes, as described in, for example, U.S. Pat. No. 6,253,099 titled "Cardiac Monitoring Electrode Apparatus and Method," the content of which is incorporated herein by reference.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more of the therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless-steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient.

Alternatively, the optional therapeutic elements can be deactivated (e.g., by a physical or a software switch), essentially rendering the therapeutic medical device a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figures 2A, 2B:
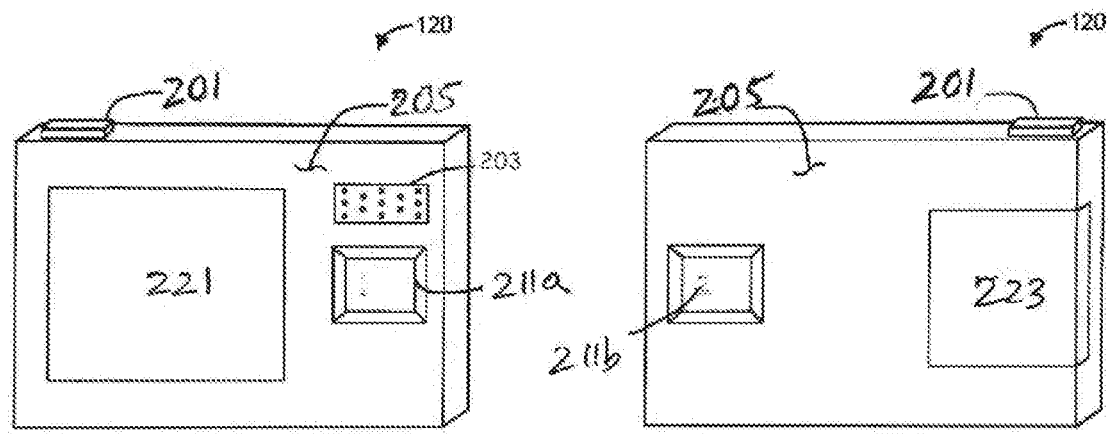
FIG. 2A depicts a first view of a medical device controller for the wearable medical device of FIG. 1.
FIG. 2B depicts a second view of a medical device controller for the wearable medical device of FIG. 1.

FIGS. 2A-B illustrate an example medical device controller 120. For example, the controller 120 includes a connector receptacle 201 for connecting the sensing and/or therapy electrode components to the controller 120. The controller 120 includes a speaker 203 for providing audio prompts to the patient and/or a bystander. The controller 120 includes circuitry as further described below with reference to FIG. 3. The circuitry is housed within a mechanical housing structure 205 to protect the circuitry and other internal components of the controller 120 from physical damage, particle ingress, and/or water ingress. The controller includes one or more response buttons 211a, 211b. A patient wearing the wearable medical device can communicate with the controller 120 via the buttons 211a, 211b. For example, if the device detects a life-threatening arrhythmia condition in the patient, the controller 120 can direct the patient to press the one or more buttons 211a, 211b. In some examples, the controller 120 can include a display screen 221. For example, the display screen 221 can be a touch-sensitive panel screen responsive to patient input in the form of touch or physical force applied to the screen. For example, the display screen 221 can display controls and/or prompts to the patient, and is responsive to the patient's touch or application of physical force on the displayed controls. The controller 120 can be powered by a removable battery 210 (see FIG. 2C below) that is housed within a battery chamber 223.

Figure 2C:
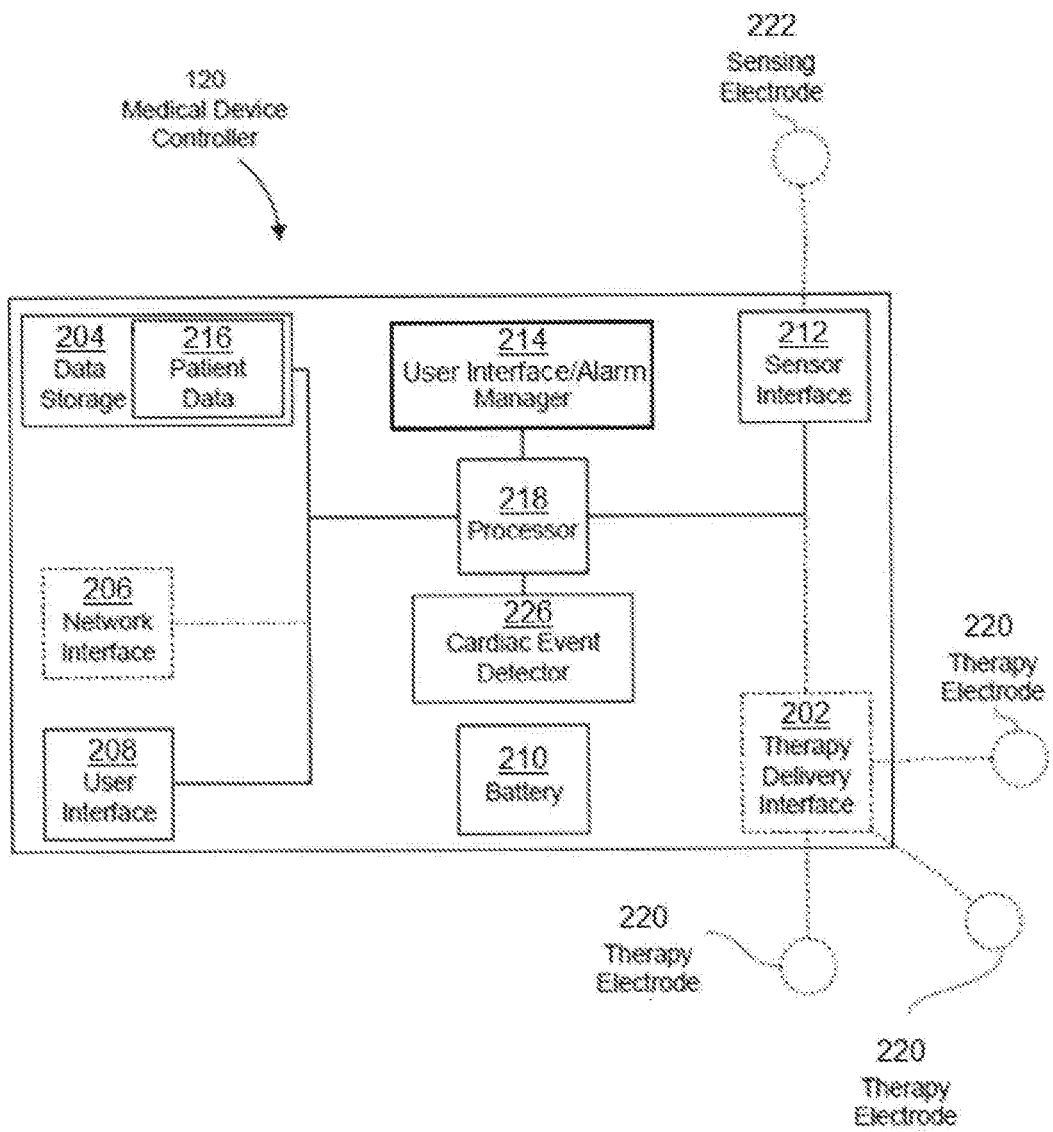
FIG. 2C depicts a component-level view of an example of a medical device controller for the wearable medical device of FIG. 1.
Figure 3:
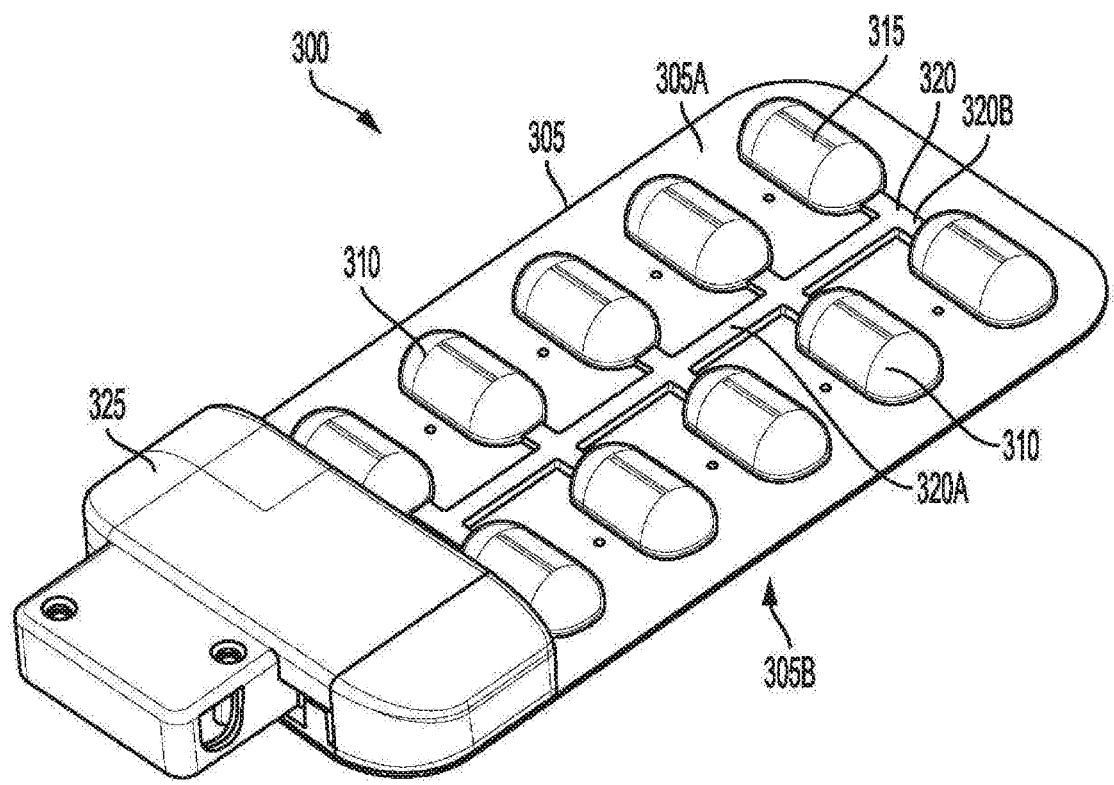
FIG. 3 depicts an example of a therapeutic electrode component.

FIG. 2C illustrates a sample component-level view of the medical device controller 120 of the medical device 100 of FIG. 1. As shown in FIG. 2C, the medical device controller 120 can include a therapy delivery interface circuit 202, a data storage 204, a network interface 206, a user interface 208, at least one battery 210, a sensor interface 212, a user interface/alarm manager 214, and least one processor 218.

The therapy delivery interface circuit 202 can be coupled to one or more electrodes 220 configured to provide therapy to the patient (e.g., therapy electrodes 114 as described above in connection with FIG. 1). For example, the therapy delivery interface circuit 202 can include, or be operably connected to, circuitry components that are configured to generate and provide the therapeutic shock. The circuitry components can include, for example, resistors, capacitors, relays and/or switches, electrical bridges such as an H-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between 350 to 500 volt surge rating and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery interface circuit 202 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance to which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage can include executable instructions that, when executed, are configured to cause the at least one processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device. The network interface 206 can include communications circuitry for transmitting data in accordance with a Bluetooth® wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the patient. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1).

The ECG electrodes 222 can monitor a patient's ECG information. For example, the ECG electrodes 222 can be galvanic (e.g., conductive) and/or capacitive electrodes configured to measure changes in a patient's electrophysiology to measure the patient's ECG information. The ECG electrodes 222 can transmit information descriptive of the ECG signals to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the at least one processor 218 to an appropriate component within the medical device controller 120. For example, if ECG data is collected by sensing electrode 222 and transmitted to the sensor interface 212, the sensor interface 212 can transmit the data to the at least one processor 218 which, in turn, relays the data to a cardiac event detector. The cardiac event data can also be stored on the data storage 204.

In certain implementations, the user interface/alarm manager 214 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The user interface/alarm manager 214 can be implemented using hardware or a combination of hardware and software. For instance, in some examples, the user interface/alarm manager 214 can be implemented as a software component that is stored within the data storage 204 and executed by the at least one processor 218. In this example, the instructions included in the alarm manager 214 can cause the at least one processor 218 to configure alarm profiles and notify intended recipients using the alarm profiles. In other examples, alarm manager 214 can be an application-specific integrated circuit (ASIC) that is coupled to the at least one processor 218 and configured to manage alarm profiles and notify intended recipients using alarms specified within the alarm profiles. Thus, examples of alarm manager 214 are not limited to a particular hardware or software implementation.

In some implementations, the at least one processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring), the at least one processor 218 can be configured to make specific logic-based determinations based on input data received, and be further configured to provide one or more outputs that can be used to control or otherwise inform subsequent processing to be carried out by the at least one processor 218 and/or other processors or circuitry with which the at least one processor 218 is communicatively coupled. Thus, the at least one processor 218 reacts to specific input stimulus in a specific way and generates a corresponding output based on that input stimulus. In some examples, the at least one processor 218 can proceed through a sequence of logical transitions in which various internal register states and/or other bit cell states internal or external to the at least one processor 218 may be set to logic high or logic low. As referred to herein, the at least one processor 218 can be configured to execute a function where software is stored in a data store coupled to the at least one processor 218, the software being configured to cause the at least one processor 218 to proceed through a sequence of various logic decisions that result in the function being executed. The various components that are described herein as being executable by the at least one processor 218 can be implemented in various forms of specialized hardware, software, or a combination thereof. For example, the processor can be a digital signal processor (DSP) such as a 24-bit DSP processor. The at least one processor can be or include a multi-core processor, e.g., having two or more processing cores. The processor can be an Advanced RISC Machine (ARM) processor such as a 32-bit ARM processor. The at least one processor can execute an embedded operating system, and include services provided by the operating system that can be used for file system manipulation, display and audio generation, basic networking, firewalling, data encryption and communications.

One embodiment of a therapeutic electrode component is illustrated in FIGS. 3-7, indicated generally as 300. The therapeutic electrode component 300 includes a base plate 305 having a first side 305A and a second side 305B opposing the first side. The second side 305B includes a conductive surface 410 (see FIG. 7). One or more repositories 310, ten in the embodiment illustrated in FIGS. 3-7, are disposed on the first side 305A of the base plate 305. The repositories 310 have an internal volume that releasably retains a conductive fluid 315.

Figure 11:
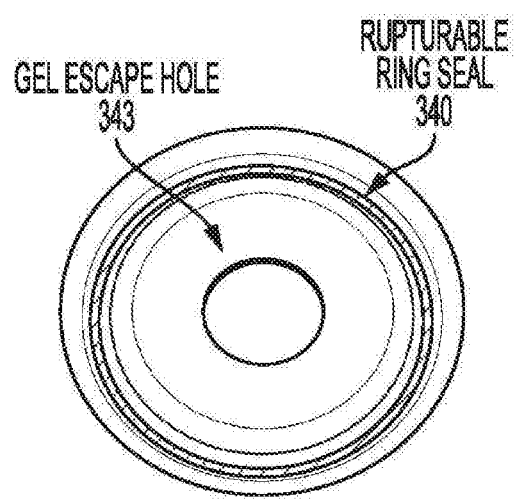
FIG. 11 depicts an example gel escape hole with a rupturable ring seal.

Referring briefly to FIG. 11, a rupturable membrane 340, e.g., in the form of a rupturable ring seal, is disposed between the internal volume of each repository 310 and the conductive surface 410 of the base plate 305. When the rupturable membrane 340 is ruptured, the fluid 315 flows from the internal volume on to the conductive surface 410 via the fluid or gel escape hole 343. The respective rupturable membranes 340 associated with each respective repository 310 are configured to rupture responsive to pressure being applied to the internal volumes of the repositories 310 so that the conductive fluid 315 can flow out of the repositories 310 and onto the conductive surface 410 of the second side 305B of the base plate 305. Each repository 310 is associated with a fluid or gel escape hole 343 to allow for the fluid or gel to escape on to the conductive surface.

Referring back to FIGS. 3-7, a conduit 320 is disposed on the base plate 305. The conduit 320 is in fluid communication between the internal volumes of each repository 310 and a coupling 330 (see FIG. 4). The conduit 320 includes a central portion 320A and branches 320B leading to each respective repository 310. The conduit provides for fluid to flow from the coupling 330 to the internal volumes of the repositories 310 to pressurize the internal volumes of the repositories 310 and cause the rupturable membrane 340 to rupture and the conductive fluid 315 to be pushed out of the repositories 310 through the ruptured rupturable membrane 340 via the fluid or gel escape holes 343.

A removable module 325 is detachably engageable with the base plate 305. As illustrated in FIGS. 5A-7, the module 325 houses a gas charge 365 and a circuit board 385. The gas charge 365 is a source of pressurized gas that, when the gas charge 365 is activated, causes gas to flow through the coupling 330 and conduit 320 to pressurize the internal volumes of the repositories 310 and cause the conductive fluid 315 to be dispensed. The circuit board 385 provides communication with an external controller, for example, medical device controller 120 illustrated in FIGS. 1, 2A, and 2B, and controls activation of the gas charge 365 and delivery of electrical therapy to a patient.

Figure 4:
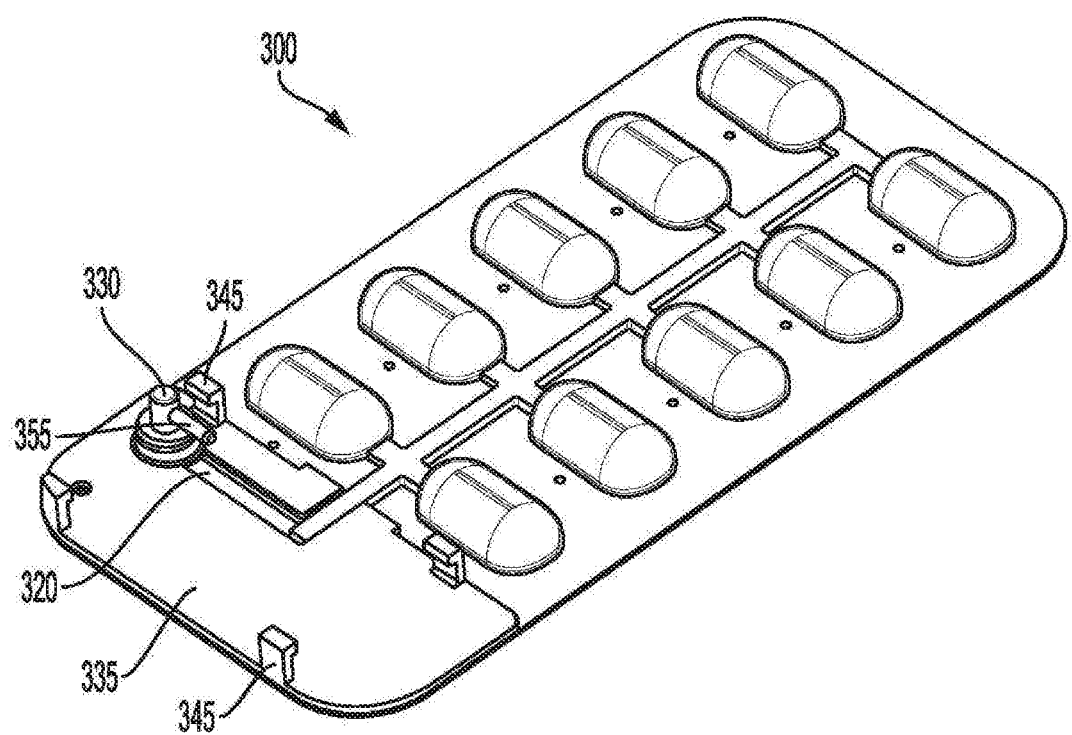
FIG. 4 depicts the therapeutic electrode component of FIG. 3 with a module including a gas charge and circuit board detached from a base plate of the therapeutic electrode component.

The therapeutic electrode component 300 is illustrated in FIG. 4 with the module 325 removed. As illustrated in FIG. 4, a cradle 335 is coupled to the first side 305A of the base plate 305. The cradle 335 is sized and shaped to releasably retain the removable module 325. The cradle 335 includes a retainer that detachably engages the module 325. In the embodiment illustrated in FIG. 4 the retainer is in the form of clips 345 that releasably engage slots 350 (see FIG. 5A) on the module 325. In other embodiments, the clips 345 may be included on the module 325 and the slots 350 on the cradle.

Also visible in FIG. 4 is the coupling 330. The coupling 330 includes a barb 355 having an internal pneumatic conduit 360 (see FIGS. 5A, 5B) that provides fluid communication between the internal volumes of the repositories 310 and the outlet of gas charge 365 via the conduit 320 when the gas charge 365 is engaged by the coupling 330. In the embodiment illustrated in FIG. 4, the barb 355 extends in a direction parallel to a plane defined by the first side 305A of the base plate 305.

Figure 5A:
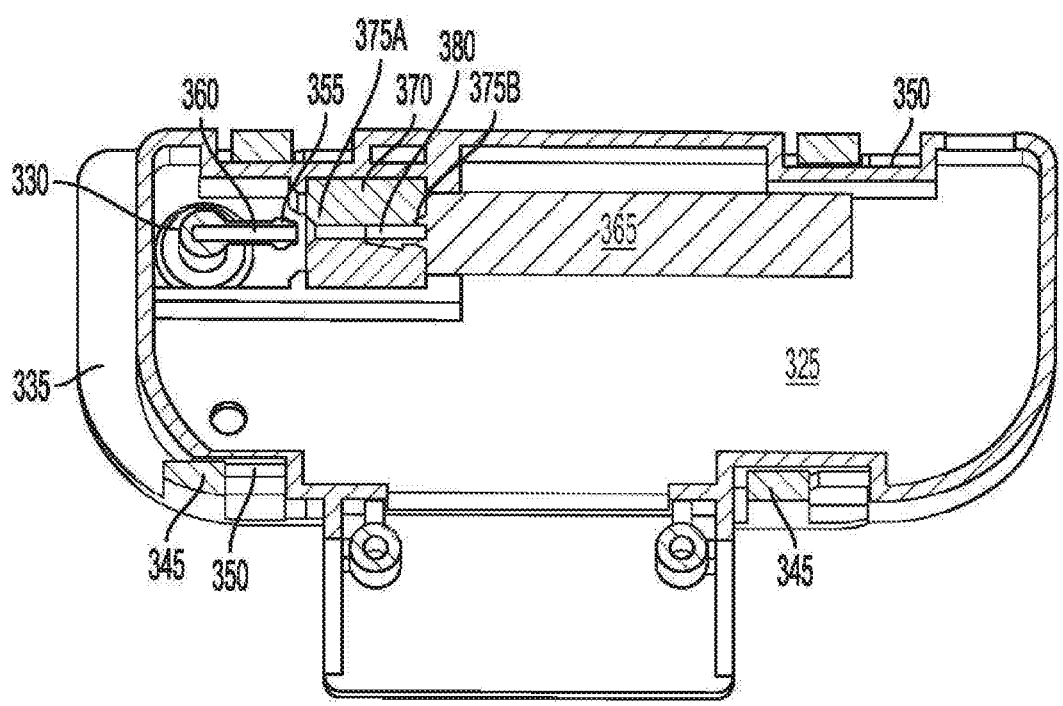
FIG. 5A depicts the module of the therapeutic electrode component of FIG. 3 partially disengaged from the base plate.
Figure 5B:
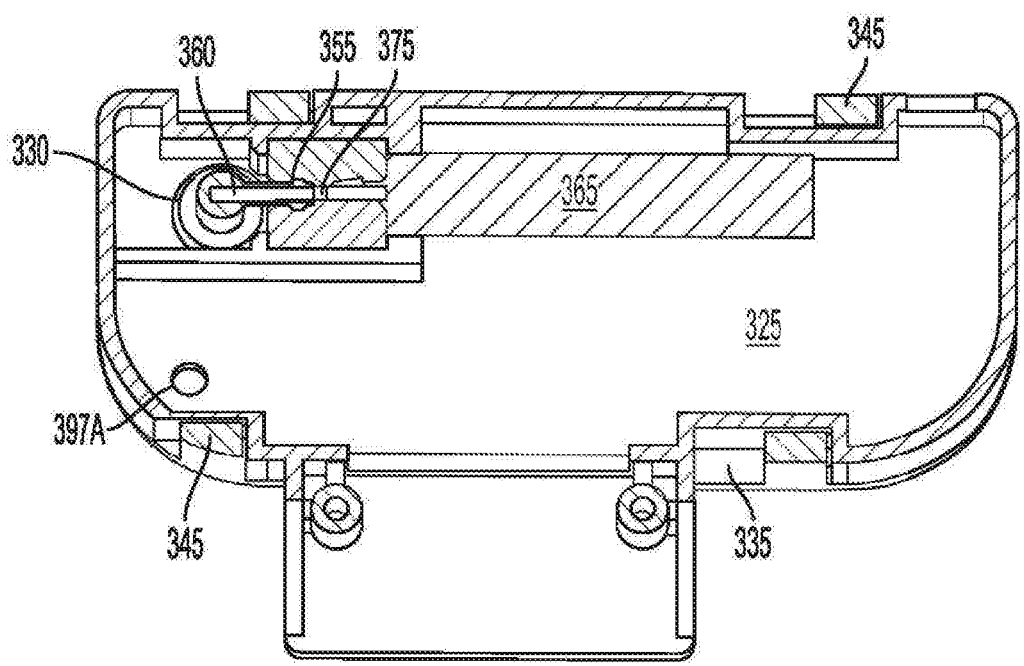
FIG. 5B depicts the module of the therapeutic electrode component of FIG. 3 engaged with the base plate.

FIGS. 5A and 5B illustrate the module 325 disposed on the cradle 335 and without its top cover. In FIG. 5A the clips 345 of the cradle are not engaged with the slots 350 on the module. If the module 325 is slid to the left in a plane defined by the surface of the first side 305A of the base plate 305 from the position shown in FIG. 5A to that shown in FIG. 5B, the clips 345 engage the slots 350 to retain the module 325 in the cradle 335. The slots 350 of the module 325 are not visible in FIG. 5B because they are underneath the clips 345.

Disposed within the module 325 is the gas charge 365. The gas charge 365 may be fixed in place in the module 325 by, for example, an adhesive or one or more fasteners. A connector 370 formed of a resilient material, for example, rubber includes a conduit 375 that has a first opening 375A that engages the barb 355 of the coupling 330 when the module 325 is in the engaged position illustrated in FIG. 5B. The conduit 375 of the connector 370 also has a second opening 375B that receives and retains an outlet 380 of the gas charge 365. The coupling 330 engages the gas charge 365 via the connector 370. The gas charge 365 may be detached from the coupling 330 by sliding the module 325 from the position illustrated in FIG. 5B to the position illustrated in FIG. 5A. When the gas charge 365 is engaged with the coupling 330 the coupling 330 provides a hermetic seal with the outlet 380 of the gas charge 365 and provides fluid communication between the internal volumes of the repositories 310 and the outlet 380 of gas charge 365.

Figure 6:
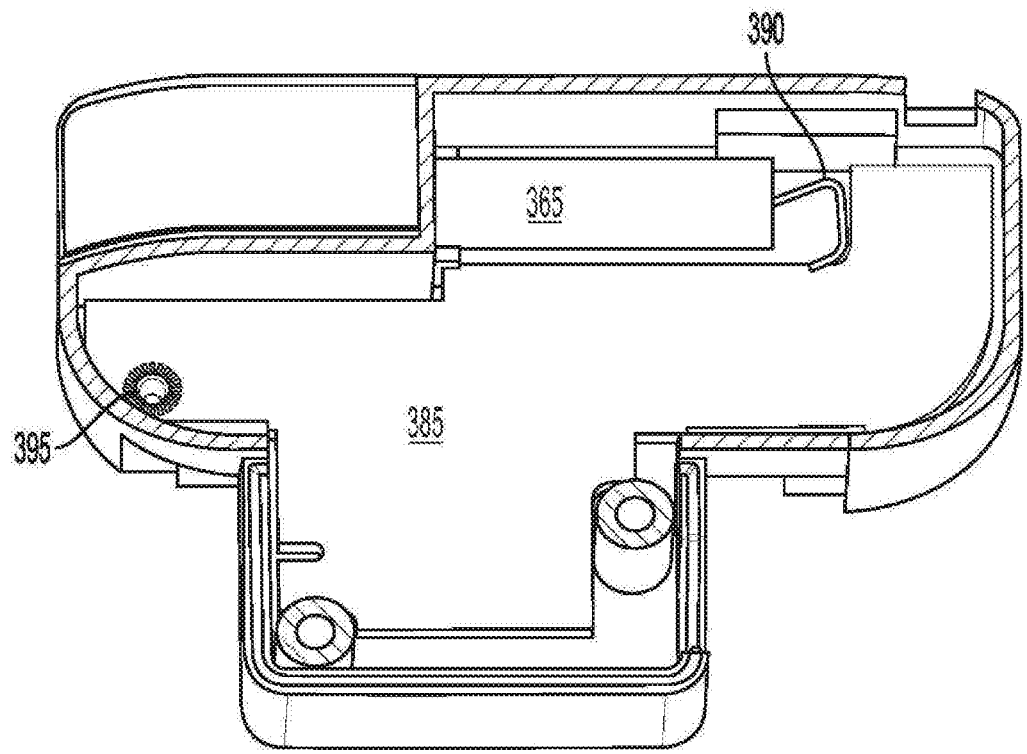
FIG. 6 depicts a circuit board and gas charge disposed within the module of the therapeutic electrode component of FIG. 3.

A circuit board 385 is also disposed within the removable module 325, as illustrated in FIG. 6. As discussed above, the circuit board 385 provides communication with an external controller, for example, medical device controller 120 illustrated in FIGS. 1, 2A, and 2B, and controls activation of the gas charge 365 and delivery of electrical therapy to a patient through the conductive surface 410 of the base plate 305 of the therapeutic electrode component 300. An electrical signal lead 390 extends from the circuit board to the gas cartridge 365 for providing an activation current to the gas charge 365. One or more apertures 395 including or surrounded by an electrical contact is provided in the circuit board 385 for outputting electrical pulses to be delivered to a patient for electrical therapy. In examples, the activation current can be at least 0.1 mA. In some applications, the activation current can be in a range from between around 0.1 mA to around 1 A. In an implementation, the activation current can be between around 0.01 A to around 0.3 A. For example, the activation current comprises a pulse of between around 1 ms and 75 seconds. In examples, the activation current comprises a pulse of around 10 ms to around 30 seconds. An operating range in which the above activation current parameters were tested is between around −25 F and 160 F.

Figure 7:
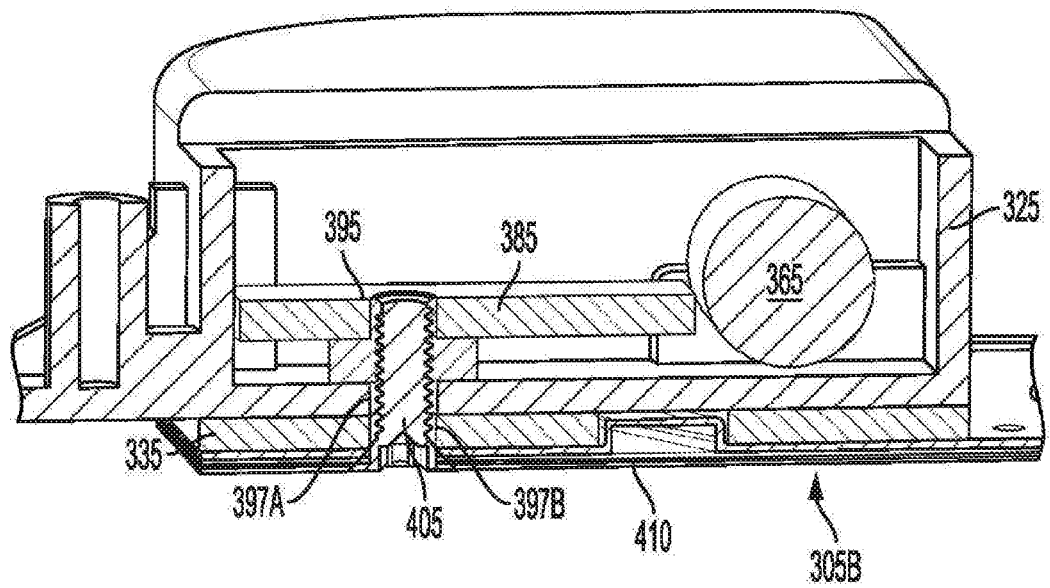
FIG. 7 illustrates a conductive fastener providing electrical connection between a conductive lower surface and the circuit board disposed within the module of the therapeutic electrode component of FIG. 3.
Figure 8A:
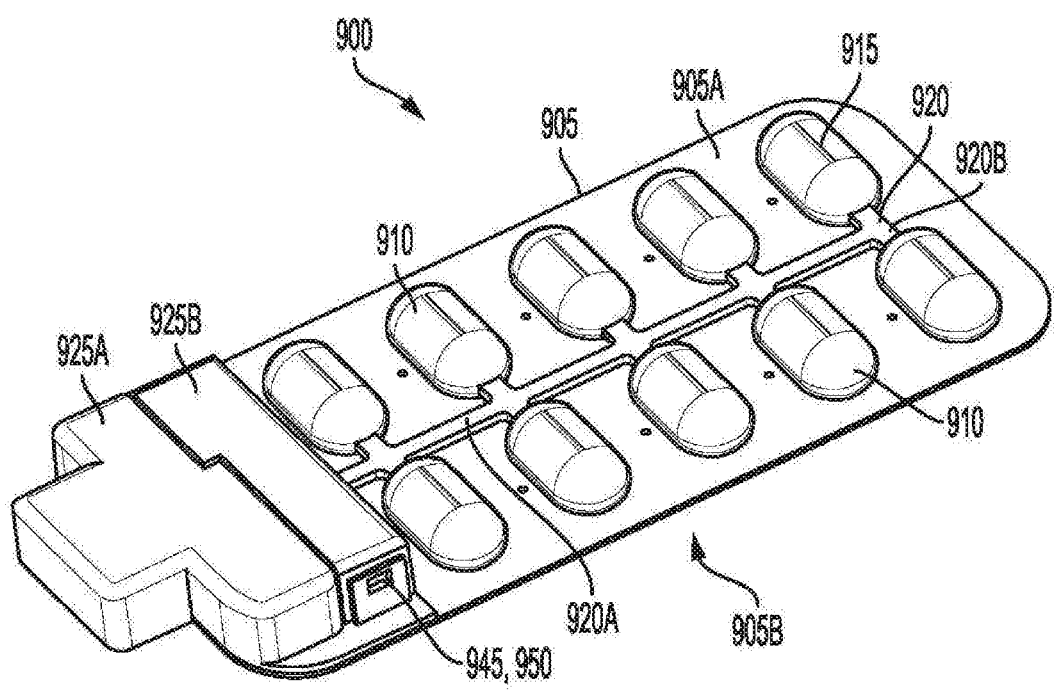
FIG. 8A depicts another example of a therapeutic electrode component.
Figure 8B:
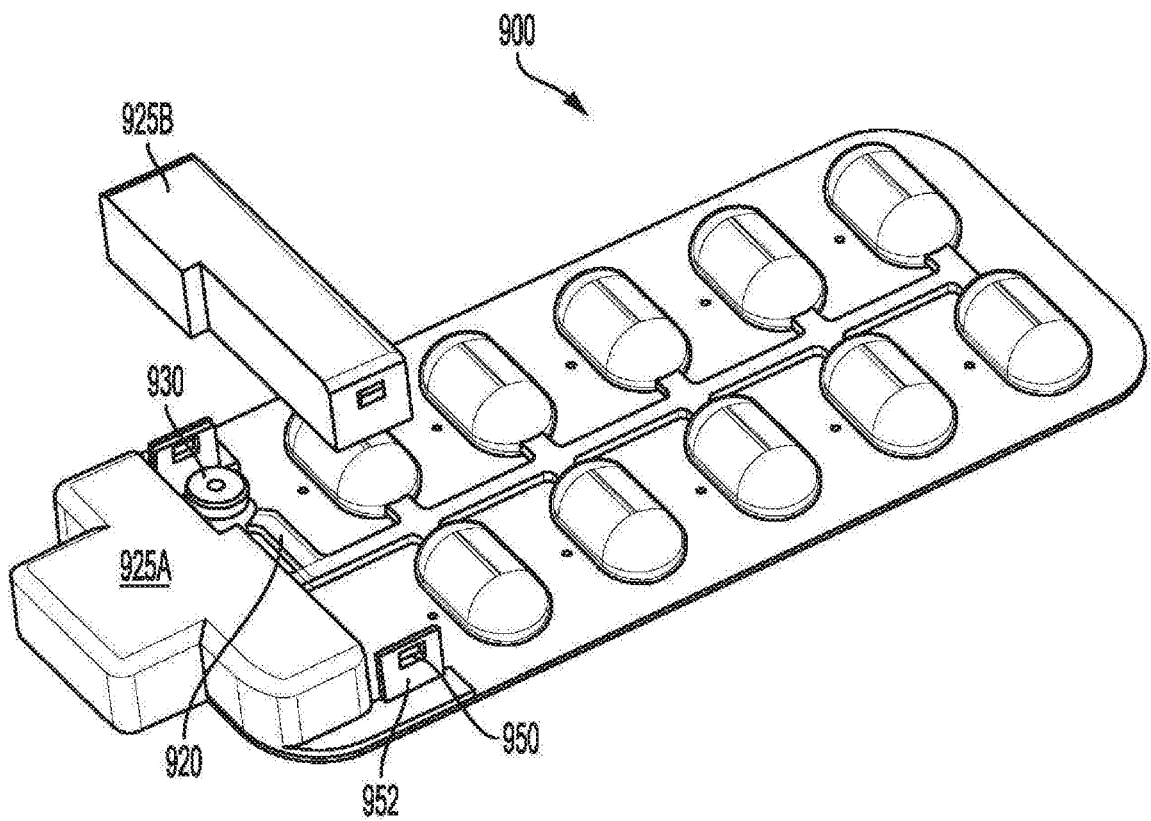
FIG. 8B depicts the therapeutic electrode component of FIG. 8A with a module including a gas charge detached from a base plate of the therapeutic electrode component.

The therapeutic electrode component 300 further includes one or more conductive fasteners 405, as illustrated in FIG. 7, that engage or pass through the one or more apertures 395 in the circuit board 385, through one or more aperture 397A in the module 325, and through one or more aperture 397B in the base plate 305. One or more of the apertures 395, 397A, 397B may be threaded to facilitate retention of the conductive fastener or fasteners 405. The conductive fastener or fasteners 405 makes an electrical connection with the electrical contact of the aperture 395 of the circuit board 385 on a first end and makes an electrical connection with the conductive surface 410 of the base plate 305 of the therapeutic electrode component 300 on a second end. The conductive fastener or fasteners 405 thus provide electrical communication between the circuit board 385 and the conductive surface 410 of the base plate 305 of the therapeutic electrode component 300. The conductive fastener or fasteners 405 is configured to deliver one of a defibrillation pulse or a pacing pulse to a subject through the conductive surface 410 of the base plate 305. The conductive fastener or fasteners 405 also secure the module 325 in place in the cradle 335 on the base plate 305. The one or more conductive fasteners 405 electrically engage the conductive surface 410 of the base plate 305 when securing module 325 to the base plate 305.

Another embodiment of a therapeutic electrode component is illustrated in FIGS. 8A-10, indicated generally at 900. The therapeutic electrode component 900 includes many of the same features as the therapeutic electrode component 300. Features of the therapeutic electrode component 900 that are similar to those of the therapeutic electrode component 300 are indicated with similar reference numbers as used for the therapeutic electrode component 300 but with the reference numbers beginning with a "9" instead of a "3." The therapeutic electrode component 900 includes, for example, a base plate 905 having a first side 905A and a second side 905B opposing the first side that corresponds with the base plate 305 of the therapeutic electrode component 300. The second side 905B includes a conductive surface 1010 (see FIG. 10) corresponding to the conductive surface 410 of the therapeutic electrode component 300. The therapeutic electrode component 900 includes repositories 910 corresponding to the repositories 310 of the therapeutic electrode component 300 disposed on the first side 905A of the base plate 905. The repositories 910 have an internal volume that releasably retains a conductive fluid 915, corresponding to the conductive fluid 315 of the therapeutic electrode component 300. The conductive fluid 915 is releasably retained within the internal volumes of the repositories by rupturable membranes corresponding to the rupturable membranes 340 of the therapeutic electrode component 300. The therapeutic electrode component 900 further includes a conduit 920 disposed on the base plate 905 that corresponds to the conduit 320 and has a central portion 920A and branches 920B, corresponding to the central portion 320A and branches 320B of the therapeutic electrode component 300.

The module of the therapeutic electrode component 900 includes a first portion 925A that is fixed to the base plate 905 and that includes a circuit board corresponding to the circuit board 385 of the therapeutic electrode component 300. The circuit board of the therapeutic electrode component 900 is electrically coupled to the conductive surface 1010 of the second side 905B of the base plate 905 of the therapeutic electrode component 900, for example, with one or more conductive fasteners corresponding to the one or more conductive fasteners 405 of the therapeutic electrode component 300.

A second portion 925B of the module of the therapeutic electrode component 900 includes a gas charge 965 corresponding to the gas charge 365 of the therapeutic electrode component 300. The second portion 925B of the module is detachably engageable with the base plate 905 and with a coupling 930 that that provides fluid communication between the internal volumes of the repositories 910 and the outlet of gas charge 965 via the conduit 920 when the gas charge 965 is engaged by the coupling 930. The second portion 925B of the module includes one or more tabs or clips 945 that releasably engage one or more apertures or slots 950 in walls 952 coupled to the base plate 905, and optionally formed integral with the first portion 925A, that define a cradle for the second portion and that removably retain the second portion 925B on the base plate 905.

Figure 9:
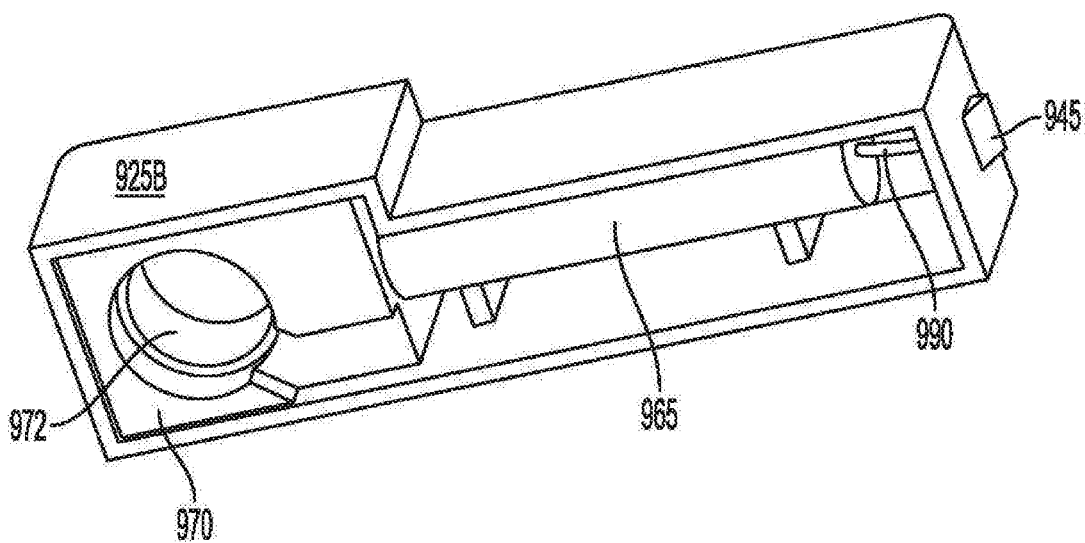
FIG. 9 depicts a gas charge disposed within the module of the therapeutic electrode component of FIG. 8A.

As illustrated in FIG. 9, the second portion 925B of the module retains a gas cartridge 965 that includes an electrical signal lead 990 that electrically connects the circuit board (e.g., similar to circuit board 385 of FIG. 6) within the first portion 925A of the module to the gas cartridge 965 for providing an activation current to the gas charge 965. The signal lead 990 can be connected to the circuit board via solder pads. For example, an electrical connection between the signal lead 990 and circuit board components can be made through a two-position connector. For example, a two-position connector can include a wire-to-wire connector with leads on one side going connected to the gas cartridge 965, and leads on the other side of the connector coupled to solder pads on the circuit board. An end of the gas cartridge 965 including the output of the gas cartridge 965 is engaged by a resilient body 970 formed of a resilient material, for example, rubber. The resilient body 970 includes a recess 972, for example, a cylindrically shaped recess in fluid communication with the outlet of the gas cartridge 965.

Figure 10:
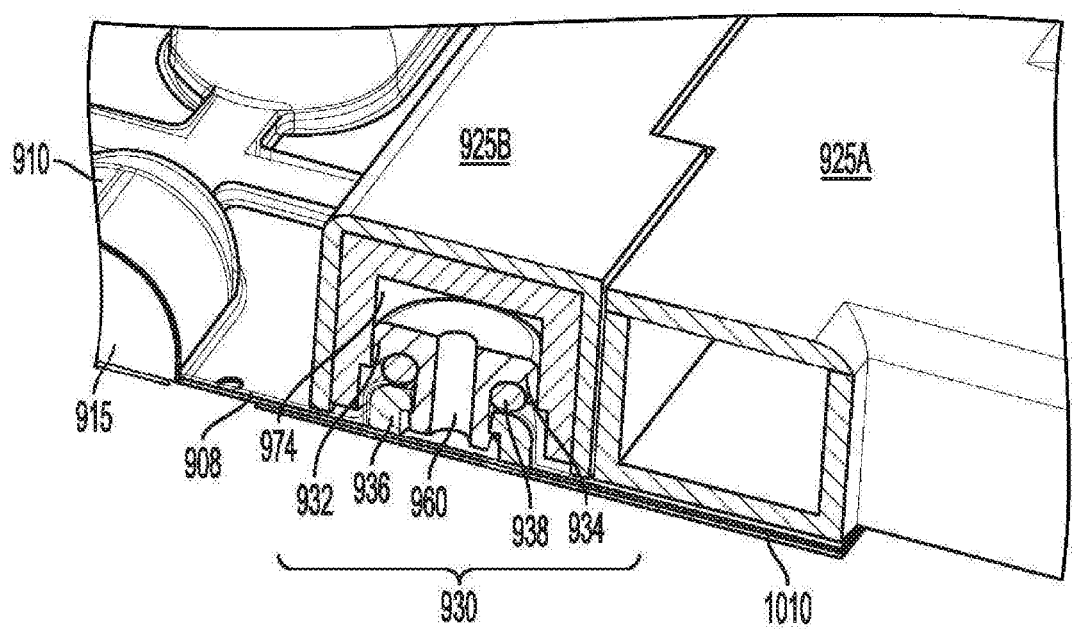
FIG. 10 depicts the module of the therapeutic electrode component of FIG. 8A engaged with a coupling on a base plate of the therapeutic electrode component.

As shown in further detail in FIG. 10, the coupling 930 includes a pneumatic header 934 that is in fluid communication with the outlet of the gas charge 965 via the connector 970. The pneumatic header 934 is received within the resilient body 970 coupled to the gas charge 965. The pneumatic header 934 is fixed to and inseparable from the base plate 905. In such an implementation, the resilient body 970 slides down over the pneumatic header making a radial seal when the gas charge 965 is installed.

The pneumatic header 934 includes an external side wall or walls 932 that are sealed to an internal wall or walls 974 of the recess 972 of the resilient body 970. In some implementations, an adhesive is dispersed within the internal wall or walls 974 of the recess 972 and the external side wall or walls 932 of the pneumatic header 934.

The pneumatic header 934 includes an internal fluid conduit 960 for flowing gas released from the gas charge 965 into the conduit 920. The coupling 930 also includes a snap ring 936 that is coupled to the first side 905A of the base plate 905. The snap ring 936 may be disposed and retained in place below a layer of plastic material 908 that covers the first side 905A of the base plate 905 and the repositories 910. In an implementation, the snap ring 936 is a fixed to and inseparable from the base plate 905. In an implementation, the snap ring 936 is sized and shaped to receive and releasably retain the pneumatic header 934. An O-ring 938 is disposed between the snap ring 936 and pneumatic header 934 when the gas charge 965 is engaged with the coupling 930 and enhances hermeticity of a seal between the snap ring 936 and pneumatic header 934. In an example, the snap ring 936 stays with the base plate when the second portion 925B is removed. In some examples, both the snap ring 936 and the O-ring 938 stay with the base plate when the second portion 925B is removed.

Another embodiment of a therapeutic electrode component is illustrated in FIGS. 12A-14B, indicated generally at 1200. The therapeutic electrode component 1200 includes many of the same features as the therapeutic electrode component 300. Features of the therapeutic electrode component 1200 that are similar to those of the therapeutic electrode component 300 are indicated with similar reference numbers as used for the therapeutic electrode component 300 but with the reference numbers beginning with a "12" instead of a "3." The therapeutic electrode component 1200 includes, for example, a base plate 1205 having a first side 1205A and a second side 1205B opposing the first side that corresponds with the base plate 305 of the therapeutic electrode component 300. The second side 1205B includes a conductive surface 1310 corresponding to the conductive surface 410 of the therapeutic electrode component 300. The therapeutic electrode component 1200 includes repositories 1210 corresponding to the repositories 310 of the therapeutic electrode component 300 disposed on the first side 1205A of the base plate 1205. The repositories 1210 have internal volumes that releasably retain a conductive fluid 1215, corresponding to the conductive fluid 315 of the therapeutic electrode component 300. The conductive fluid 1215 is releasably retained within the internal volumes of the repositories by rupturable membranes corresponding to the rupturable membranes 340 of the therapeutic electrode component 300. The therapeutic electrode component 1200 further includes a conduit 1220 disposed on the base plate 1205 that corresponds to the conduit 320 and has a central portion 1220A and branches 1220B, corresponding to the central portion 320A and branches 320B of the therapeutic electrode component 300.

A removable module 1225 is detachably engageable with the base plate 1205. The module 1225 houses a gas charge 1265 and a circuit board 1285, corresponding to the gas charge 365 and circuit board 385, respectively, of the therapeutic electrode component 300. The gas cartridge 1265 that includes an electrical signal lead 1290 that electrically connects the circuit board 1285 within the module 1225 to the gas cartridge 1265 for providing an activation current to the gas charge 1265. The module 1225 is illustrated without a cover to show the gas charge 1265 and circuit board 1285 contained within, but in use, would include a cover. When the module 1225 is removably secured to the base plate 1205, the circuit board 1285 of the therapeutic electrode component 1200 may be electrically coupled to the conductive surface 1310 of the second side 1205B of the base plate 1205 of the therapeutic electrode component 1200, for example, with one or more conductive fasteners corresponding to the one or more conductive fasteners 405 of the therapeutic electrode component 300.

Figure 12A:
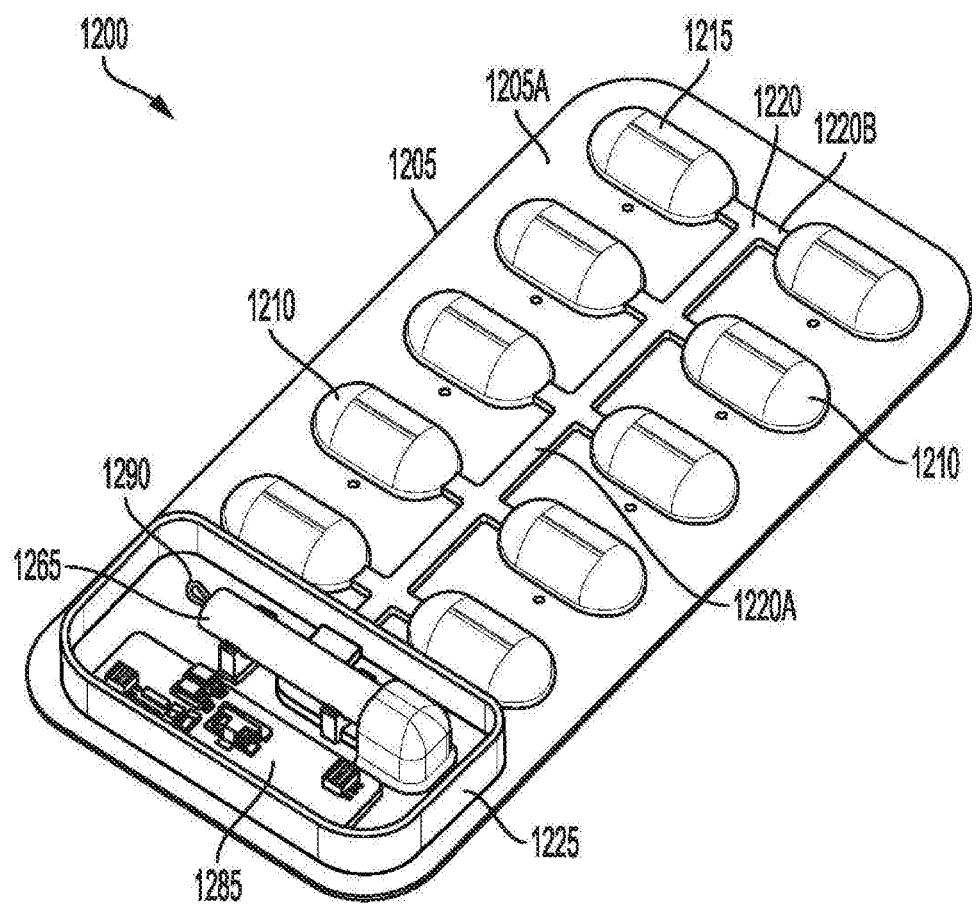
FIG. 12A depicts another example of a therapeutic electrode component.
Figure 12B:
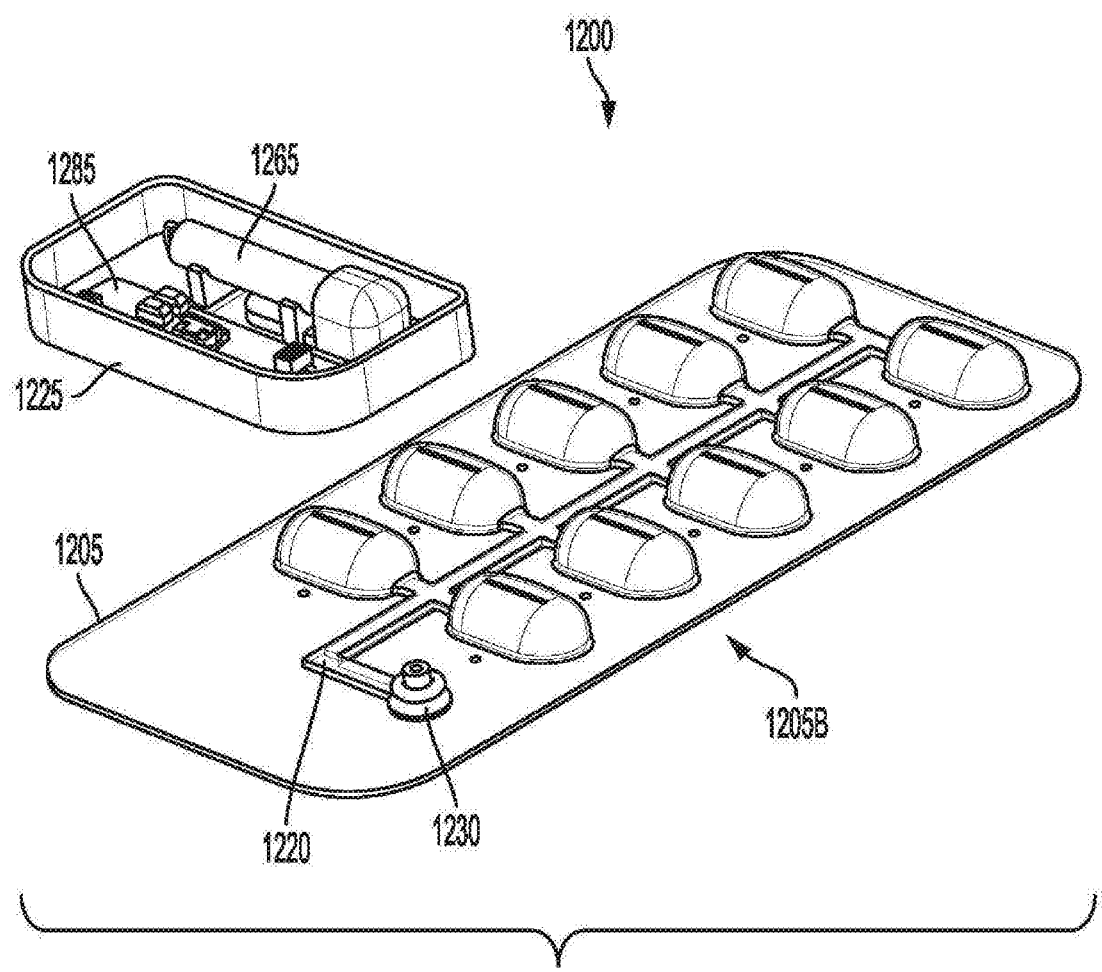
FIG. 12B depicts the therapeutic electrode component of FIG. 12A with a module including a gas charge and circuit board detached from a base plate of the therapeutic electrode component.

The module 1225 is detachably engageable with the base plate 1205 and from a coupling 1230 that that provides fluid communication between the internal volumes of the repositories 1210 and the outlet of gas charge 1265 via the conduit 1220 when the gas charge 1265 is engaged by the coupling 1230. The therapeutic electrode component 1200 is illustrated in FIG. 12B with the module 1225 removed and the coupling 1230 visible. The module 1225 is removed and placed onto the base plate 1205 by pulling or pushing the module 1225 in a direction normal to a plane defined by the first side 1205A or second side 1205B of the base plate 1205. Installing or removing the module 1225 from the base plate 1205 causes an aperture 1275 in a lower surface 1225B of the module 1225 to engage or disengage the coupling 1230.

Figure 13:
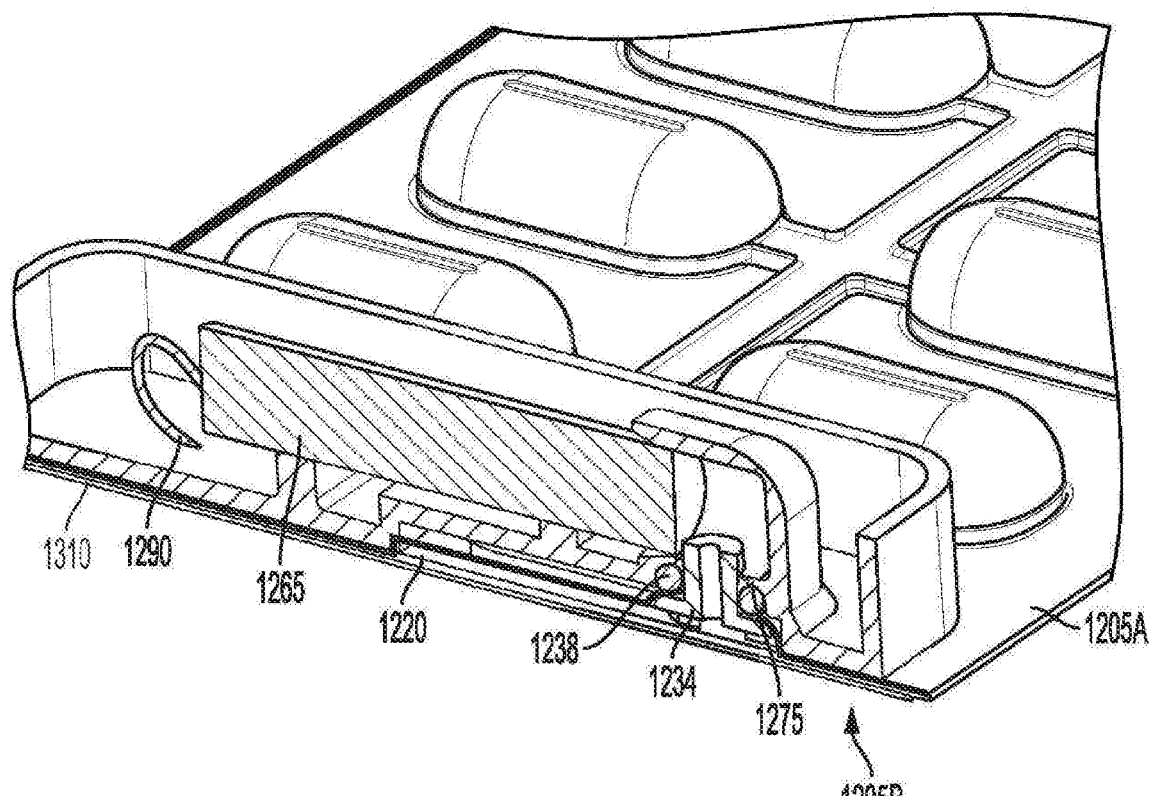
FIG. 13 depicts the module of the therapeutic electrode component of FIG. 12A engaged with a coupling on a base plate of the therapeutic electrode component.
Figure 14A:
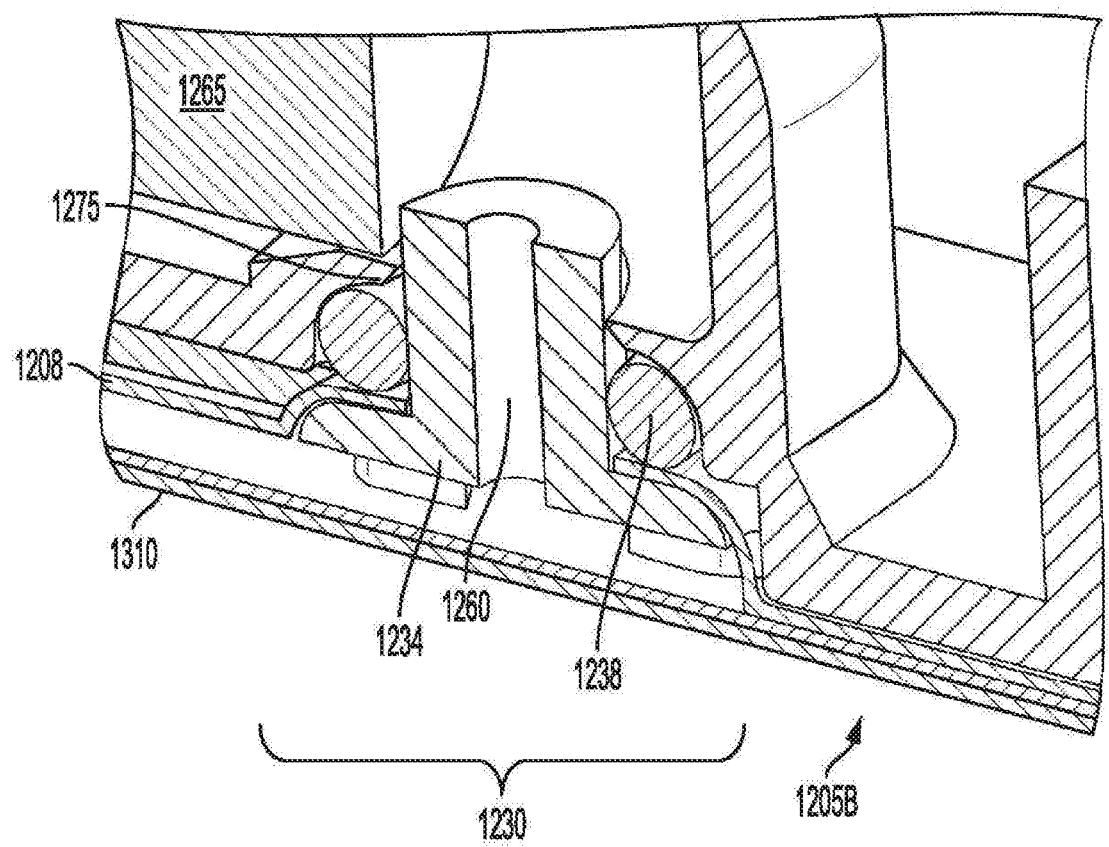
FIG. 14A is an enlarged view of the area of engagement of the module of the therapeutic electrode component of FIG. 12A with the coupling on the base plate of the therapeutic electrode component.
Figure 14B:
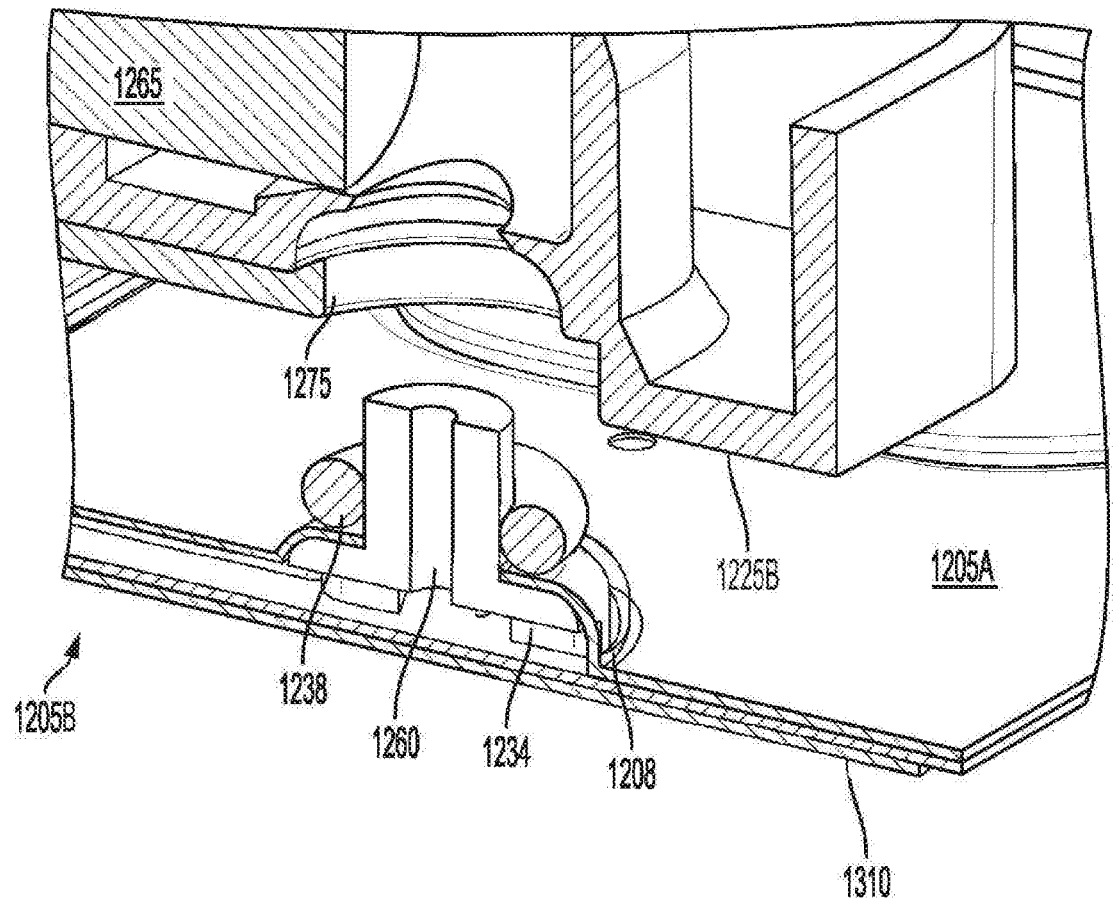
FIG. 14B is an enlarged view of the area of engagement of the module of the therapeutic electrode component of 12A with the coupling on the base plate of the therapeutic electrode component with the module being unengaged with the coupling.

As illustrated in further detail in FIGS. 13, 14A, and 14B, the coupling 1230 includes a post 1234 disposed on the first side 1205A of the base plate 1205 and including a pneumatic conduit 1260 configured to provide the fluid communication between the internal volume of the repositories 1210 and the outlet of gas charge 1265 when the gas charge 1265 is engaged by the coupling 1230. The post 1234 is sized and shaped to engage the aperture 1275 in the module 1225. The post 1234 may include a flange portion that is disposed below and retained in place by a layer of plastic material 1208 that covers the first side 1205A of the base plate 1205 and the repositories 1210. An O-ring 1238 is disposed between a neck of the pneumatic conduit 1260 defined in the post 1234 and the aperture 1275 in the module 1225. The O-ring 1238 enhances hermeticity of a seal between the pneumatic conduit 126 defined in the post 1234 and module 1225.

The module 1225 can be secured to the base plate 1205 with one or more screws. For example, the one or more screws can include threaded inserts or self-tapping screws. In examples, the module 1225 can be secured to the base plate 1205 with screws that are inserted from the conductive side of the base plate 1205 and pass through the layers of the base plate 1205 and tighten into corresponding screw bosses in the module 1225.

Another embodiment of a therapeutic electrode component is illustrated in FIGS. 15A-16C, indicated generally at 1500. The therapeutic electrode component 1500 includes many of the same features as the therapeutic electrode component 300. Features of the therapeutic electrode component 1500 that are similar to those of the therapeutic electrode component 300 are indicated with similar reference numbers as used for the therapeutic electrode component 300 but with the reference numbers beginning with a "15" instead of a "3." The therapeutic electrode component 1500 includes, for example, a base plate 1505 having a first side 1505A and a second side 1505B opposing the first side that corresponds with the base plate 305 of the therapeutic electrode component 300. The second side 1505B includes a conductive surface 1610 corresponding to the conductive surface 410 of the therapeutic electrode component 300. The therapeutic electrode component 1500 includes repositories 1510 corresponding to the repositories 310 of the therapeutic electrode component 300 disposed on the first side 1505A of the base plate 1505. The repositories 1510 have internal volumes that releasably retain a conductive fluid 1515, corresponding to the conductive fluid 315 of the therapeutic electrode component 300. The conductive fluid 1515 is releasably retained within the internal volumes of the repositories by rupturable membranes corresponding to the rupturable membranes 340 of the therapeutic electrode component 300. The therapeutic electrode component 1500 further includes a conduit 1520 disposed on the base plate 1505 that corresponds to the conduit 320 and has a central portion 1520A and branches 1520B, corresponding to the central portion 320A and branches 320B of the therapeutic electrode component 300.

Figure 16A:
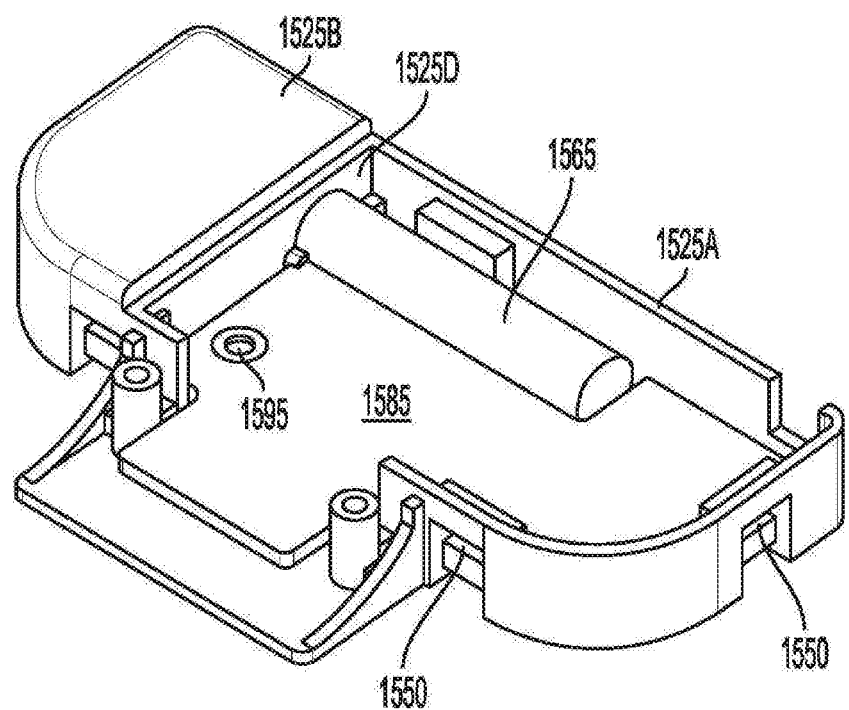
FIG. 16A depicts the gas charge and circuit board disposed within the module of the therapeutic electrode component of FIG. 15A.

The therapeutic electrode component 1500 includes a module 1525 detachably engaged with the base plate 1505. The module 1525 includes a first body 1525A and a second body 1525B. As illustrated in FIGS. 16A and 16C, the first body 1525A houses a gas charge 1565 and a circuit board 1585 which correspond to the gas charge 365 and circuit board 385 of the therapeutic electrode component 300.

Figure 15A:
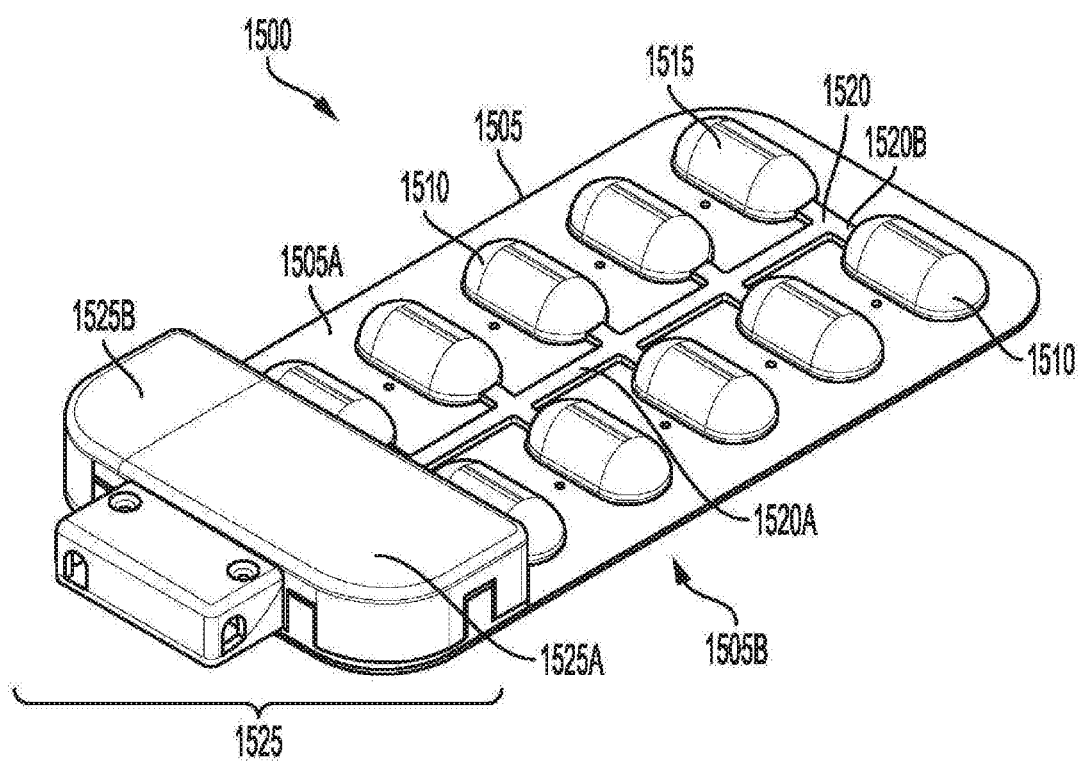
FIG. 15A depicts another example of a therapeutic electrode component.
Figure 15B:
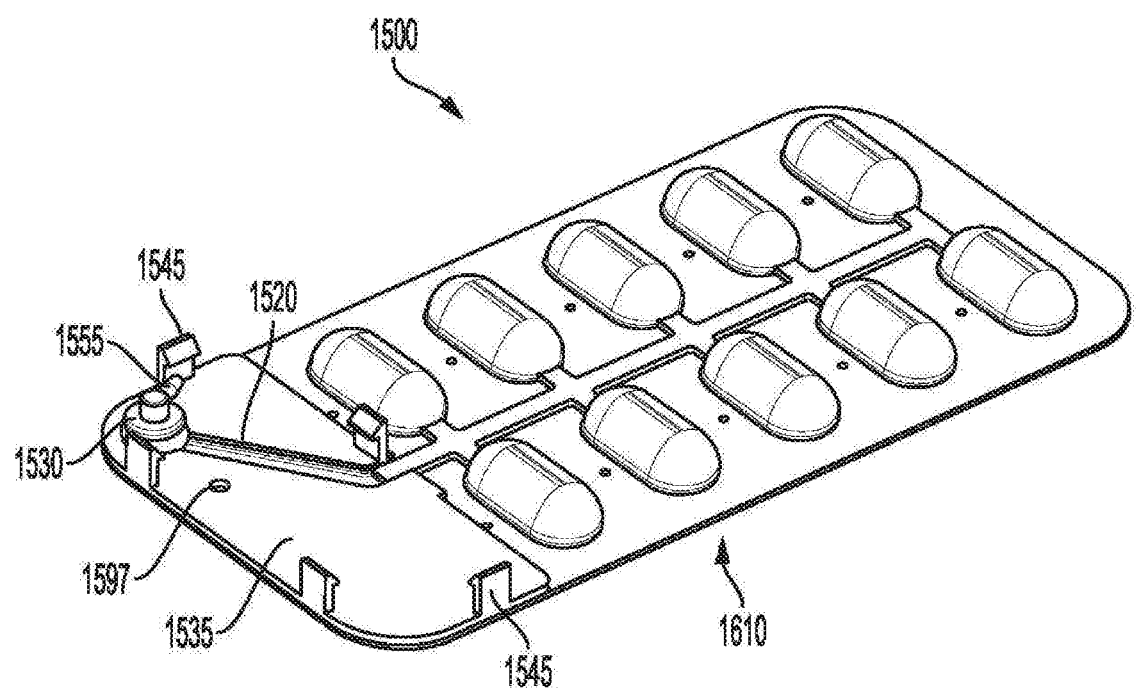
FIG. 15B depicts the therapeutic electrode component of FIG. 15A with a module including a gas charge and circuit board detached from the base plate of the therapeutic electrode component.

The therapeutic electrode component 1500 is illustrated in FIG. 15B with the module 1525 removed. As illustrated in FIG. 15B, a cradle 1535 is coupled to the first side 1505A of the base plate 1505. The cradle 1535 is sized and shaped to releasably retain the removable module 1525. The cradle 1535 includes a retainer that detachably engages the module 1525. In the embodiment illustrated in FIG. 15B the retainer is in the form of clips 1545 that releasably engage recesses 1550 (see FIGS. 16A, 16B) on the module 1525. To engage the module 1525 with the cradle 1535 and base plate 1505, the module 1525 is pushed downward in a direction normal to a plane defined by the base plate 1505 into the cradle 1535 until the clips 1545 of the cradle 1535 engage the recesses 1550 of the module 1525. The module 1525 may be removed from the cradle 1535 and base plate 1505 by pulling upward on the module 1525 with sufficient force to cause the clips 1545 of the cradle 1535 to disengage the recesses 1550 of the module 1525 and release the module 1525 from the cradle 1535. In other embodiments, the clips 1545 may be included on the module 1525 and the recesses 1550 on the cradle clips. A portion of the conduit 1520 may be formed by a channel defined in the cradle 1535.

Also visible in FIGS. 15B and 16C is a coupling 1530. The coupling 1530 includes a barb 1555 that provides fluid communication between the internal volumes of the repositories 1510 and the outlet of gas charge 1565 via the conduit 1520 when the gas charge 1565 is engaged by the coupling 1530. In the embodiment illustrated in FIGS. 15B and 16C, the barb 355 extends in a direction parallel to a plane defined by the first side 305A of the base plate 305. The module 1525 may be removed and replaced from the cradle 1535 and base plate 1505 without damaging the coupling 1530.

Figure 16B:
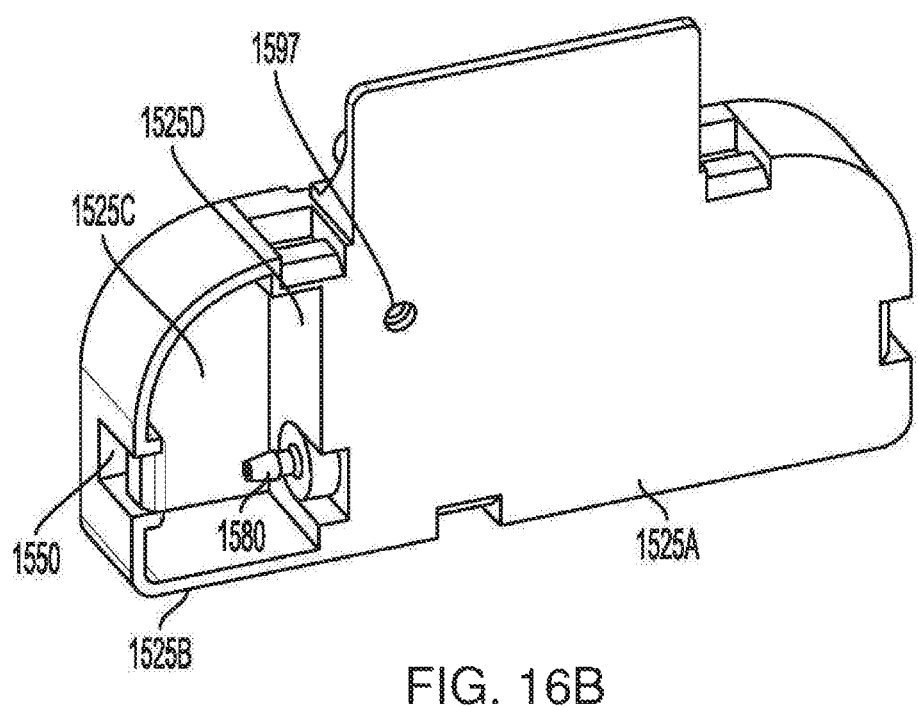
FIG. 16B depicts an underside of the module of the therapeutic electrode component of FIG. 15A.
Figure 16C:
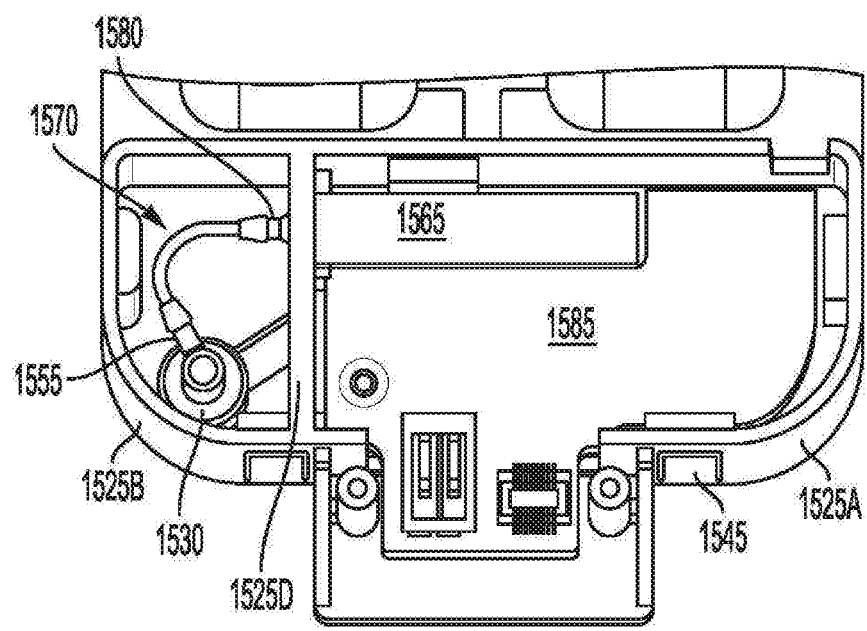
FIG. 16C depicts module of the therapeutic electrode component of FIG. 15A disposed on the base plate and the outlet of the gas charge pneumatically connected to a coupling on the base plate.

As illustrated in FIGS. 16B and 16C, an outlet 1580 of the gas charge 1565 extends through a wall 1525D separating an internal volume of the first body 1525A of the module 1525 from a chamber 1525C defined in the second body 1525B of the module 1525. A short length of pneumatic tubing 1570 engages the barb 1555 of the coupling 1530 and the outlet 1580 of the gas charge 1565 and provides fluid communication between the internal volumes of the repositories 1510 and the outlet 1580 of gas charge 1565 via the coupling 1530 and conduit 1520.

The circuit board 1585 includes one or more apertures 1595, corresponding to the one or more apertures 395 of the therapeutic electrode component 300, that include or are surrounded by an electrical contact for outputting electrical pulses to be delivered to a patient for electrical therapy. One or more conductive fasteners, corresponding to the one or more conductive fasteners 405 of the therapeutic electrode component 300, may engage or pass through the one or more apertures 1595 in the circuit board 1585, through one or more aperture 1597 in the cradle 1535, one or more apertures (not shown) in the module 1525, and through one or more apertures (not shown) in the base plate 1505. One or more of the apertures in the circuit board 1585, base plate 1505, and/or module 1525 may be threaded to facilitate retention of the conductive fastener or fasteners. The conductive fastener or fasteners makes an electrical connection with the electrical contact of the aperture 1595 of the circuit board 1585 on a first end and makes an electrical connection with the conductive surface 1610 of the base plate 1505 of the therapeutic electrode component 1500 on a second end. The conductive fastener or fasteners thus provide electrical communication between the circuit board 1585 and the conductive surface 1610 of the base plate 1505 of the therapeutic electrode component 300. The conductive fastener or fasteners is configured to deliver one of a defibrillation pulse or a pacing pulse to a subject through the conductive surface 1610 of the base plate 1505. The conductive fastener or fasteners may also help secure the module 1525 in place in the cradle 1535 on the base plate 1505. The one or more conductive fasteners electrically engage the conductive surface 1610 of the base plate 1505 when securing module 1525 to the base plate 1505.

Figure 17A:
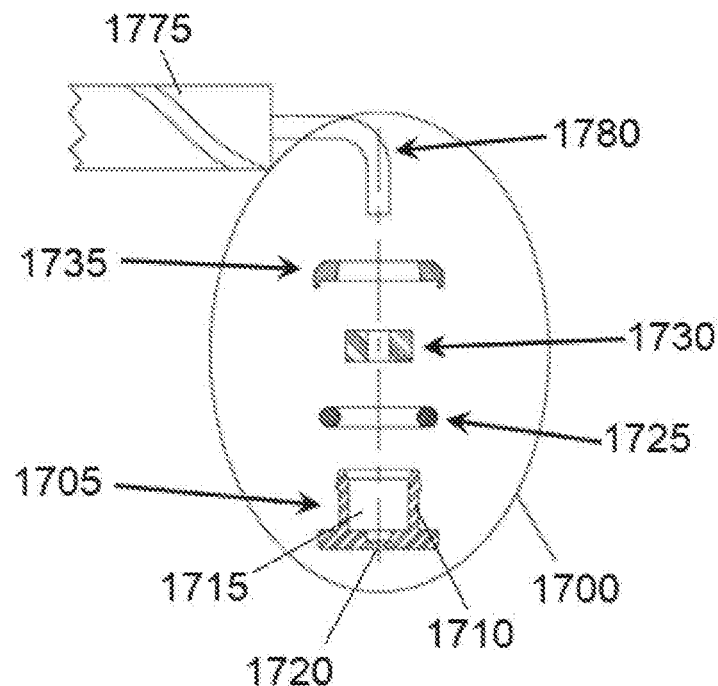
FIG. 17A depicts another connection mechanism for pneumatically coupling a gas charge to a base plate of a therapeutic electrode component in an exploded view.
Figure 17B:
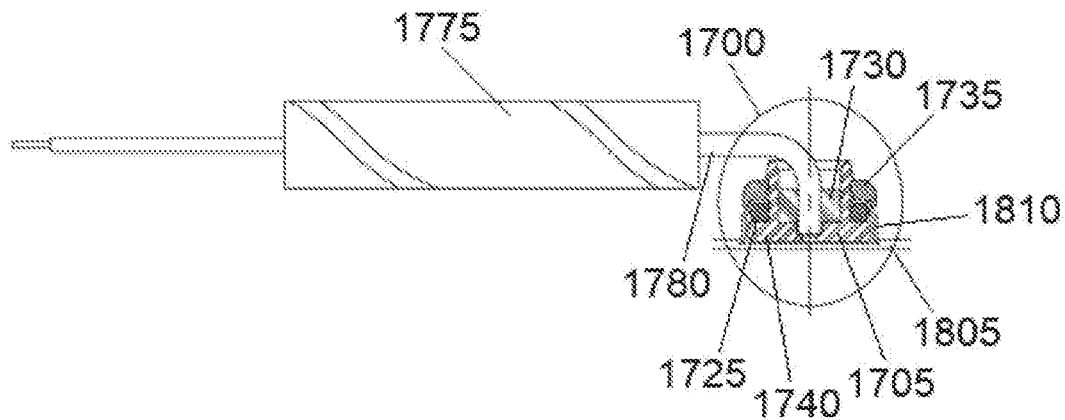
FIG. 17B depicts the mechanism of FIG. 17A in an assembled state.

Another example of a coupling for pneumatically connecting a gas charge to a conduit in fluid communication with internal volumes of one or more repositories in a therapeutic electrode component as disclosed herein is illustrated in FIGS. 17A and 17B, indicated generally at 1700. The coupling 1700 is illustrated along with a gas charge 1775 having an outlet 1780 in the form of a tube, for example, a stainless steel tube, in an exploded view in FIG. 17A, and in an assembled view in FIG. 17B. The coupling includes a feed-through 1705 that has a neck 1710 defining an interior volume 1715. The feed-through 1705 also includes an aperture 1720 to provide fluid communication between the gas charge 1775 and one or more conductive fluid repositories via a conduit of a therapeutic electrode component as disclosed herein. An O-ring 1725 fits around and surrounds the neck 1710 of the feed-through 1705. The coupling 1700 further includes a washer 1730 formed of a resilient material that surrounds a length of the outlet 1780 of the gas charge 1775 and is configured to be retained within the internal volume 1715 of the neck 1710 of the feed-thorough 1705. A snap ring 1735 couples to the feed through 1705 and traps the O-ring 1725 between the snap ring 1735 and the feed-through 1705. The internal wall of the neck 1710 of the feed-through 1705 may compress the washer 1730 to facilitate forming a hermetic seal between the outlet 1780 of the gas charge 1775 and the aperture 1720 of the feed-through 1705. The snap ring 1735 may compress the neck 1710 of the feed-through 1705 to help compress the washer 1730. In some embodiments, the coupling 1700 may be secured to a base plate 1805 of a therapeutic electrode component as disclosed herein by a plastic film 1810 that covers the O-ring 1725 and flange portion 1740 of the feed-through 1705.

Figure 18A:
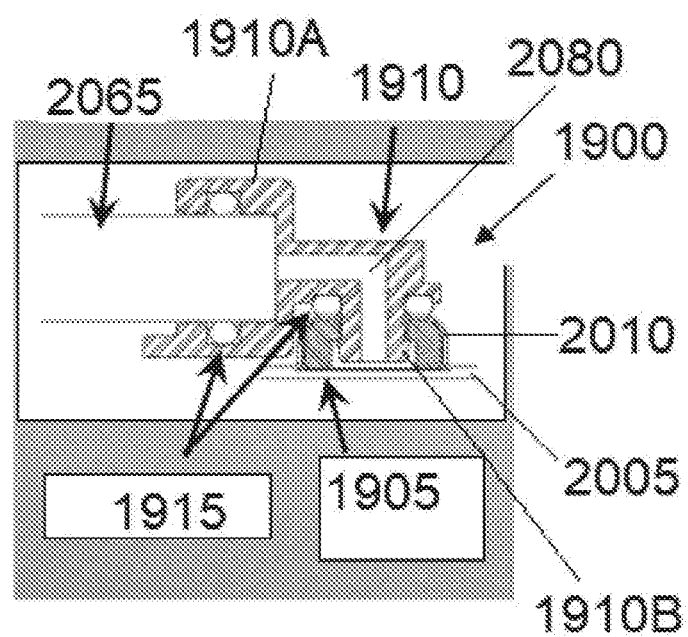
FIG. 18A depicts another connection mechanism for pneumatically coupling a gas charge to a base plate of a therapeutic electrode component.

Another example of a coupling for pneumatically connecting a gas charge to a conduit in fluid communication with internal volumes of one or more repositories in a therapeutic electrode component as disclosed herein is illustrated in FIG. 18A, indicated generally at 1900. The coupling 1900 includes a snap ring 1905 coupled to the first side of the base plate 2005 of a therapeutic electrode component as disclosed herein. The snap ring 1905 may be secured to the base plate 2005 by a layer of plastic material 2010 that covers the surface of the base plate 2005. The coupling 1900 also includes a feed-through 1910 including a base 1910A that surrounds an end portion of the gas charge 2065 and the outlet 2080 of the gas charge 2065, and a barb 1910B extending from the base 1910A that is configured to releasably engage the snap ring 1905. An O-ring 1915 is disposed between the base 1910A and the snap ring 1905 when the barb 1910B is engaged with the snap ring 1905. The O-ring 1915 enhances hermeticity of a seal between the feed-through 1910 and snap ring 1905. A second O-ring 1915 may be disposed on an inner wall or in a recessed region of the base 1910A to facilitate forming a hermetic seal between the gas charge 2065 and the feed-through 1910.

When sealing with O-rings in the manner described herein, a hermetic seal is achieved. An O-ring is a doughnut-shaped object or torus. In application, the opposite sides of an O-ring are squeezed between the walls of the space into which the O-ring is installed. The resulting zero clearance within the space provides an effective seal, blocking the flow of liquids or gases through the space's internal passage. An O-ring is typically defined by its dimensions (e.g., based on inside hole diameter, ID, and cross section), durometer (Shore A hardness), and material composition. For example, the O-ring can be from any of the following materials. In implementations herein, the O-ring installation incorporates initial O-ring compression. At atmospheric pressure, the inherent resiliency of the compressed O-ring provides the seal. As system pressure activates the seal, the O-ring is forced to the low pressure side of the space. Designed to deform, the O-ring thus fill the diametrical clearance and blocks leakage to form the hermetic seal. For example, the O-ring can be Buna-N/Nitrile rubber, a copolymer of butadiene and acrylonitrile. Nitrile combines resistance to petroleum-based oils and fuels, silicone greases, hydraulic fluids, water and alcohols. It has a low compression set, high tensile strength and high abrasion resistance. The O-ring can be made from a compound in the ethylene-propylene (EPM/EPDM) family. Such materials feature good resistance to such polar solvents as ketones (e.g., acetone). EPM/EPDM is resistant to steam (e.g., up to 400° F.), hot water, silicone oils and greases, dilute acids and alkalis, alcohols and automotive brake fluids. Ethylene propylene can provide extended temperature range of around −76° F. to around +350° F. The O-ring can be made from a compound in the silicone family. Silicone material is resistant to high, dry heat. Silicones are fungus resistant, odorless, tasteless, non-toxic elastomers and possess high-resistance to the aging effects of both sunlight and ozone. The O-ring can be made from a compound in the neoprene family. Neoprene features moderate resistance to petroleum oils, good resistance to ozone, sunlight and oxygen aging, relatively low compression set, good resilience, reasonable cost, and high resistance to ammonia. The O-ring can be made from a compound in the fluorocarbon family. Such materials can combine high-temperature resistance with wide chemical agent compatibility. Fluorocarbon compounds feature good resistance to petroleum products and solvents and good high-temperature compression set characteristics. The O-ring can be made from a compound in the fluorosilicone family. Such materials combine the good high and low temperature stability of silicones with the fuel, oil and solvent resistance of fluorocarbons. These compounds feature good compression set and resilience properties. The compounds are suitable for exposure to air, sunlight, ozone, chlorinated and aromatic hydrocarbons. For example, the O-rings are standard AS-568 sizes (Aerospace Size Standard for O-rings from the Society of Automotive Engineers).

In examples, the hermetic seal as described herein can be tested in a following manner. For example, the test as described herein can be carried out as an engineering or validation testing of therapy electrode components containing a detachable gas generator. For example, failure analysis testing on units returned from the field can be tested by inserting a hypodermic needle through the laminate into the air channel and sealing around the entrance point with a cyanoacrylate adhesive. The hypodermic needle can then be attached to a regulated air source. The therapy electrode can be placed into a container filled with water. Using the regulator, the air pressure can be increased until a leak is detected.

In examples, a Pass/Fail test can be used for production. For example, a burst test for the pressurized receptacles can be set to determine that the receptacles can withstand pressures of at least between 40 psi and 60 psi. For example, a burst test for the pressurized receptacles can be set to a maximum of at least 60 psi. For example, a burst test for the pressurized receptacles can be set to a maximum of at least 50 psi. For example, a burst test for the pressurized receptacles can be set to a maximum of at least 50 psi.

In examples, a potential production/service test for therapy electrode components containing a detachable gas generator can be as follows. A sealable port or, in some examples, the same port that the detachable gas generator interfaces with the receptacles can serve as the test port. A ring-seal test can be performed where the base plate laminate can be pressurized to at least 12 psi for a prescribed period of time, 3 seconds, before releasing the pressure. This test can help eliminate weak ring seals that could potentially leak in the field. In implementations, the 12 psi pressure supply can be introduced for 3 seconds and then the supply can be cut off to monitor for a period of time, between 15-30 seconds, for a pressure drop. A pressure drop can indicate a leak. After this period has ended, the pressure can be released.

Figure 18B:
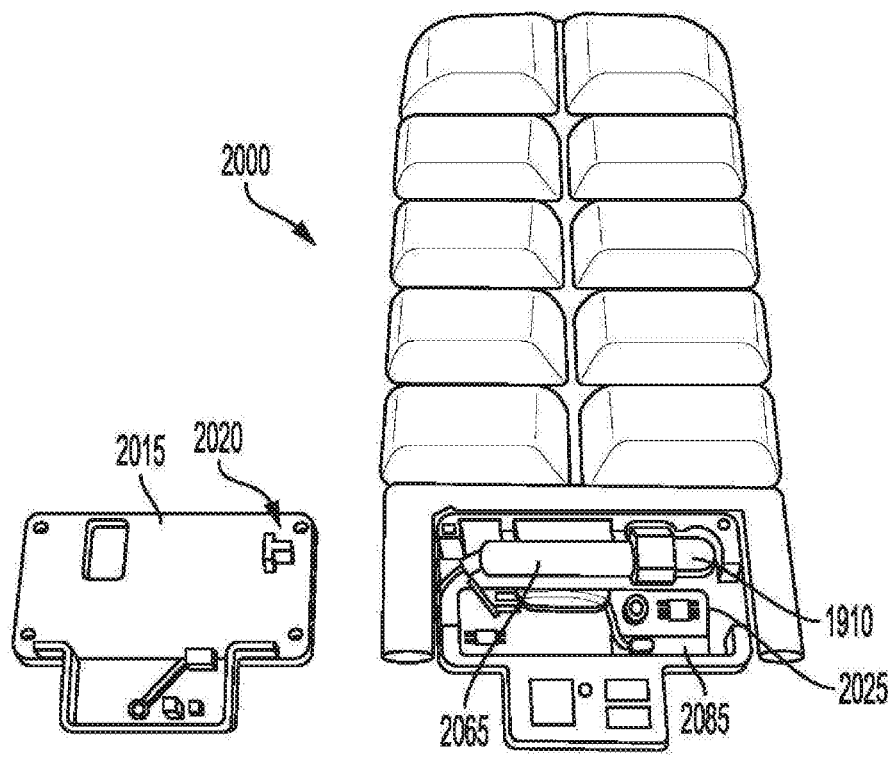
FIG. 18B depicts the mechanism of FIG. 18A disposed in an example of a therapeutic electrode component.
Figure 18C:
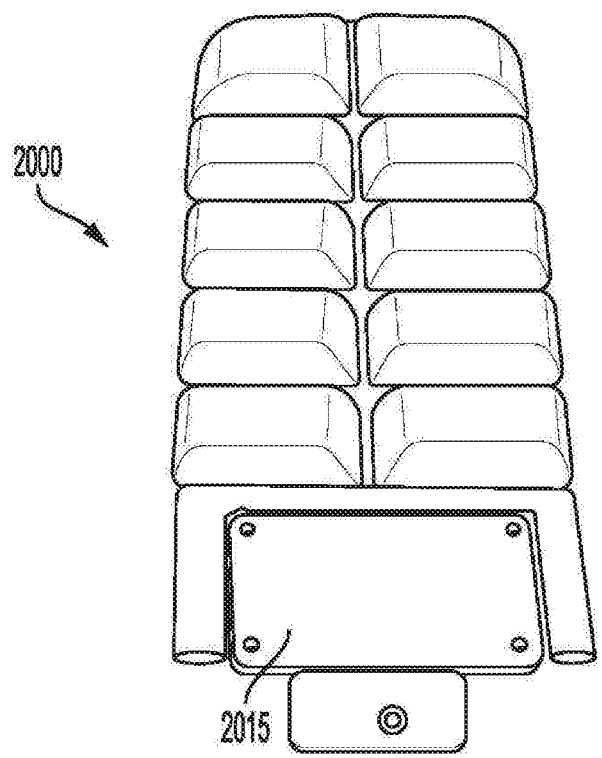
FIG. 18C depicts the therapeutic electrode component of FIG. 18B in an assembled state.

FIG. 18B illustrates an example of a therapeutic electrode component 2000 including a gas charge 2065 coupled to the therapeutic electrode component 2000 with a coupling 1900 as illustrated in FIG. 18A. In FIG. 18B, a feed-through 1910 of the coupling 1900 is visible. The gas charge 2065 and a circuit board 2085 are disposed in a cavity 2025 defined in an end of the therapeutic electrode component 2000. A lid 2015 is used to cover the cavity 2025 in the therapeutic electrode component 2000. The lid 2020 includes a retainer 2020, which functions to keep the gas charge from becoming mechanically disengaged (e.g., prevent the gas charge from "popping out") when activated. For example, the retainer 2020 can mechanically engage with the gas charge 2065 when the lid 2015 is secured. In an implementation, the retainer 2020 can be positioned over the gas charge 2065 to reduce movement of the gas charge 2065 within the cavity 2025 and further keep it from becoming mechanically disengaged when activated. FIG. 18C illustrates the therapeutic electrode component 2000 with the lid 2015 attached.

In a first example use case, a user wears a wearable therapeutic device including a garment as illustrated in FIG. 1 and multiple therapeutic electrode components 300 as illustrated in FIGS. 3-7 removably disposed within the garment. The user receives a notification, either from the controller of the wearable therapeutic device or from a provider of the wearable therapeutic device, that the conductive fluid in one or more of the therapeutic electrode components 300 has reached its expiration date. The user acquires one or more new base plates including receptacles filled with fresh conductive fluid and including the conduit, cradle, and coupling as illustrated in FIG. 4. The user removes the conductive fastener or fasteners from the one or more therapeutic electrode components that have expired conductive fluid and slides the respective modules including the respective gas charges and circuit boards out of the respective cradles. The user then slides the respective modules including the respective gas charges and circuit boards into the cradles of the replacement base plate sand secures the modules in the cradles with the one or more conductive fasteners. The user then replaces the one or more therapeutic electrode components including the replacement base plates back into their respective locations in the garment. The old base plates with the expired conductive fluid may be discarded or returned to the provider.

A similar use case to the first example use case described above would apply to a user who wears a wearable therapeutic device including a garment as illustrated in FIG. 1 and multiple therapeutic electrode components 1200 as illustrated in FIGS. 12A-14B or multiple therapeutic electrode components 1500 as illustrated in FIGS. 15A-16C removably disposed within the garment. A difference would be that the user removes and replaces the module by lifting the module off of the base plate and replaces the module on the base plate via movement of the module in a direction normal to a plane defined by the first or second surfaces of the base plate. If the user wears a wearable therapeutic device including therapeutic electrode components 1500 the user would disconnect the pneumatic tubing 1570 prior to removing the module from the old base plate and would disengage the clips 1545 from the module to allow it to be removed. The user would press the module into the cradle of the replacement base plate until the clips of the cradle of the replacement base plate engage the module. The user would reconnect the pneumatic tubing between the coupling of the replacement base plate and the outlet of the gas cartridge in the module prior to placing the therapeutic electrode component with the replacement base plate back into the garment.

In a second example use case, a user again wears a wearable therapeutic device including a garment as illustrated in FIG. 1 and multiple therapeutic electrode components 300 as illustrated in FIGS. 3-7 removably disposed within the garment. The user receives a notification, for example, from the provider of the wearable therapeutic device that one or more of the gas charges in one or more of the therapeutic electrode components disposed in the garment have been discovered to belong to a batch that has been experiencing failures, for example, failures to release gas after receiving an activation current. The provider sends the user one or more replacement modules including circuit boards and gas charges from a different batch. The user removes the conductive fastener or fasteners from the one or more therapeutic electrode components that have the suspected bad gas charges and slides the respective old modules out of the respective cradles. The user then slides the new modules including the replacement gas charges and circuit boards into the respective cradles of the base plates of the respective therapeutic electrode components and secures the modules in the cradles with the one or more conductive fasteners. The user then replaces the one or more therapeutic electrode components including the replacement modules back into their respective locations in the garment. The old modules with the suspected bad gas charges may be discarded or returned to the provider.

A similar use case to the second example use case described above would apply to a user who wears a wearable therapeutic device including a garment as illustrated in FIG. 1 and multiple therapeutic electrode components 1200 as illustrated in FIGS. 12A-14B or multiple therapeutic electrode components 1500 as illustrated in FIGS. 15A-16C removably disposed within the garment. A difference would be that the user removes and replaces the module by lifting the module off of the base plate and replaces the module on the base plate via movement of the module in a direction normal to a plane defined by the first or second surfaces of the base plate. If the user wears a wearable therapeutic device including therapeutic electrode components 1500 the user would disconnect the pneumatic tubing 1570 prior to removing the old module from the old base plate and would disengage the clips 1545 from the old module to allow it to be removed. The user would press the new module into the cradle until the clips engage the new module. The user would reconnect the pneumatic tubing between the coupling and the outlet of the gas cartridge in the new module prior to placing the therapeutic electrode component with the new module back into the garment.

In a third example use case, the user may wear a wearable therapeutic device including a garment as illustrated in FIG. 1 and multiple therapeutic electrode components 900 as illustrated in FIGS. 8A-10 removably disposed within the garment. In the therapeutic electrode components 900 the removable module includes a gas charge, but not a circuit board. In a situation similar to that described in the first example use case above, the user would receive a replacement base plate (or more than one) including receptacles filled with fresh conductive fluid and including the conduit, cradle, module first portion 925A including a new circuit board, and coupling as illustrated in FIG. 8B. The user removes the therapeutic electrode component including the expired conductive fluid from the garment, lifts the module second portion 925B including the gas charge out of cradle of the old therapeutic electrode component, and presses the module second portion 925B into the cradle of the replacement base plate until the one or more tabs or clips 945 on the module engage the one or more apertures or slots 950 in the walls 952 coupled to the base plate 905. The user then replaces the therapeutic electrode component including the replacement base plate and old module second portion 925B into the garment.

In a fourth example use case, the user may wear a wearable therapeutic device including a garment as illustrated in FIG. 1 and multiple therapeutic electrode components 900 as illustrated in FIGS. 8A-10 removably disposed within the garment. In the therapeutic electrode components 900 the removable module includes a gas charge, but not a circuit board. In a situation similar to that described in the second example use case above, the user would receive a replacement module (or more than one) including a circuit board and gas charge from a different batch. The user removes the therapeutic electrode component including the suspect gas charge from the garment, lifts the module second portion 925B including the suspect gas charge out of cradle of the old therapeutic electrode component, and presses the replacement module second portion 925B into the cradle of the base plate until the one or more tabs or clips 945 on the module engage the one or more apertures or slots 950 in the walls 952 coupled to the base plate 905. The user then replaces the therapeutic electrode component including the replacement gas charge and old base plate into the garment.

It should be appreciated that in any of the example use cases described above, the user of the medical device may be capable of performing the replacement of the portions of the therapy electrode component(s). In other examples, these operations may be performed by a provider of the medical device, for example, by the user sending a wearable medical device including one or more of the therapy electrode components to a provider for service or refurbishment.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A therapeutic electrode component for application of electrical stimulus to a subject and for allowing reuse of non-destroyed portions of a therapeutic electrode in application of electrical stimulus to a subject, the component comprising:
    a base plate having a first side and a second side opposing the first side, the second side having a conductive surface;
    a repository having an internal volume configured to releasably retain a conductive fluid, the repository disposed on the first side of the base plate;
    a rupturable membrane disposed between the internal volume of the repository and the conductive surface of the base plate;
    a coupling disposed on the base plate, the coupling configured to detachably engage a gas charge, the gas charge being detachable from the coupling without causing destruction of at least the gas charge, the coupling further configured to provide a hermetic seal with an outlet of the gas charge, and to provide fluid communication between the internal volume of the repository and the outlet of gas charge when the gas charge is engaged by the coupling; and
    a retainer configured to detachably secure the gas charge to the base plate.

2. The therapeutic electrode component of claim 1, wherein the gas charge is detachable from the coupling without causing destruction of at least the base plate, the repository, and the rupturable membrane.

3. The therapeutic electrode component of claim 1, wherein the coupling comprises a barb including an internal pneumatic conduit configured to provide the fluid communication between the internal volume of the repository and the outlet of gas charge when the gas charge is engaged by the coupling.

4. The therapeutic electrode component of claim 3, further comprising a connector formed of a resilient material and including a conduit having a first opening configured to receive and releasably retain the barb and a second opening configured to receive and retain the outlet of the gas charge.

5. The therapeutic electrode component of claim 1, wherein the coupling comprises:
a snap ring coupled to the first side of the base plate; and
a pneumatic header in fluid communication with the outlet of the gas charge, the snap ring being configured to releasably retain the pneumatic header.

6. The therapeutic electrode component of claim 5, wherein the pneumatic header is retained within a resilient body coupled to the gas charge.

7. The therapeutic electrode component of claim 1, wherein the coupling comprises:
a feed-though disposed on the first side of the base plate including a neck defining an internal volume;
a washer formed of a resilient material that surrounds a length of the outlet of the gas charge and is configured to be retained within the internal volume of the neck of the feed-through;
an O-ring surrounding the neck of the feed-through; and
a snap ring that couples to the feed through and traps the O-ring between the snap ring and the feed-through.

8. The therapeutic electrode component of claim 1, wherein the gas charge is disposed within a module that is detachably engageable with the base plate, and the coupling includes a post disposed on the first side of the base plate and including a pneumatic conduit configured to provide the fluid communication between the internal volume of the repository and the outlet of gas charge when the gas charge is engaged by the coupling, the post configured to engage an aperture in the module.

9. The therapeutic electrode component of claim 1, wherein the gas charge is disposed within a module that is detachably engageable with the base plate, and wherein the module is configured to couple to the first side of the base plate by sliding the module in a plane defined by a surface of the first side of the base plate into a cradle coupled to the first side of the base plate.

10. The therapeutic electrode component of claim 9, wherein the retainer includes one or more conductive fasteners that pass through the base plate and engage one or more respective apertures in the module.

11. The therapeutic electrode component of claim 10, wherein the one or more conductive fasteners electrically engage the conductive surface of the base plate when securing module to the base plate.

12. The therapeutic electrode component of claim 1, further comprising one or more conductive fasteners, the one or more conductive fasteners configured to deliver one of a defibrillation pulse or a pacing pulse to the subject through the conductive surface of the base plate.

13. The therapeutic electrode component of claim 12, wherein the defibrillation pulse comprises a biphasic current pulse of between about 0 and 150 Amps and the pacing pulse comprises a current of between about 0 mAmps to about 200 to mAmps.

14. The therapeutic electrode component of claim 1, wherein the gas charge is disposed within a module that is detachably engageable with the base plate, and the therapeutic electrode component further comprises:

a circuit board disposed within the module and configured to control activation of the gas charge; and
signal leads in electrical communication between the circuit board and the gas charge and configured to deliver an activation current to the gas charge.

15. The therapeutic electrode component of claim 1, wherein the gas charge is disposed within a module that is detachably engageable with the base plate, the module being configured to couple to the first side of the base plate by moving the module in a direction perpendicular to a plane defined by a surface of the first side of the base plate on to the first side of the base plate.

16. The therapeutic electrode component of claim 1, further comprising a conduit disposed on the base plate providing fluid communication between the coupling and the internal volume of the repository.

17. The therapeutic electrode component of claim 16, wherein the repository comprises a plurality of separate chambers each releasably retaining a volume of the conductive fluid and in fluid communication with the conduit.

18. The therapeutic electrode component of claim 16, wherein the rupturable membrane is configured to rupture responsive to delivery of gas from the gas charge to the internal volume of the repository through the conduit.

19. The therapeutic electrode component of claim 18, wherein the repository is configured to release the conductive fluid onto the conductive surface of the base plate responsive to delivery of gas from the gas charge to the internal volume of the repository through the conduit.

20. A wearable therapeutic device for allowing reuse of non-destroyed portions of a therapeutic electrode in application of electrical stimulus to a subject, comprising:
a garment configured to be worn about the subject;
at least one therapeutic electrode component configured to be removably retained by the garment;
circuitry configured to provide a therapeutic pulse of energy to the at least one therapeutic electrode component; and
at least one processor operatively coupled to the circuitry and the at least one therapeutic electrode component, wherein the at least one therapeutic component comprises:
a base plate having a first side and a second side opposing the first side, the second side having a conductive surface;
a repository having an internal volume configured to releasably retain conductive fluid, the repository disposed on the first side of the base plate;
a rupturable membrane disposed between the internal volume of the repository and the conductive surface of the base plate;
a coupling disposed on the base plate, the coupling configured to detachably engage a gas charge, the gas charge being detachable from the coupling without causing destruction of at least the gas charge, the coupling further configured to provide a hermetic seal with an outlet of the gas charge, and to provide fluid communication between the internal volume of the repository and the outlet of gas charge when the gas charge is engaged by the coupling; and
a retainer configured to detachably secure the gas charge to the base plate.

21. The wearable therapeutic device of claim 20, wherein the gas charge is detachable from the coupling without causing destruction of at least the base plate, the repository, and the rupturable membrane.

22. The wearable therapeutic device of claim 20, further comprising one or more conductive fasteners, the one or more conductive fasteners configured to deliver one of a defibrillation pulse or a pacing pulse to the subject through the conductive surface of the base plate.

23. The wearable therapeutic device of claim 22, wherein the defibrillation pulse comprises a biphasic current pulse of between about 0 and 150 Amps and the pacing pulse comprises a current of between about 0 mAmps to about 200 to mAmps.

24. The wearable therapeutic device of claim 20, wherein the gas charge is disposed within a module that is detachably engageable with the base plate, and the therapeutic electrode component further comprises:
   a circuit board disposed within the module and configured to control activation of the gas charge; and
   signal leads in electrical communication between the circuit board and the gas charge and configured to deliver an activation current to the gas charge.

25. The wearable therapeutic device of claim 20, further comprising a conduit disposed on the base plate providing fluid communication between the coupling and the internal volume of the repository.

26. The wearable therapeutic device of claim 25, wherein the repository comprises a plurality of separate chambers each releasably retaining a volume of the conductive fluid and in fluid communication with the conduit.

\* \* \* \* \*